US012661067B2

(12) United States Patent
Gormley et al.

(10) Patent No.: US 12,661,067 B2
(45) Date of Patent: Jun. 23, 2026

(54) ROBOTIC ARTIFICIAL INTELLIGENCE NASAL/ORAL/RECTAL ENTERIC TUBE

(71) Applicant: THE BRIGHAM AND WOMEN'S HOSPITAL, INC., Boston, MA (US)

(72) Inventors: William B. Gormley, Boston, MA (US); Brittany Stopa, Boston, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 913 days.

(21) Appl. No.: 17/027,364

(22) Filed: Sep. 21, 2020

(65) Prior Publication Data

US 2021/0059607 A1    Mar. 4, 2021

Related U.S. Application Data

(63) Continuation-in-part of application No. PCT/US2020/023793, filed on Mar. 20, 2020.

(Continued)

(51) Int. Cl.
*A61B 5/00*        (2006.01)
*A61B 34/20*       (2016.01)
(Continued)

(52) U.S. Cl.
CPC .......... *A61B 5/6852* (2013.01); *A61B 5/0013* (2013.01); *A61B 5/0075* (2013.01);
(Continued)

(58) Field of Classification Search
None
See application file for complete search history.

(56) References Cited

U.S. PATENT DOCUMENTS 5,363,838 A      11/1994   George
10,791,933 B2    10/2020   Goldring et al.
(Continued)

FOREIGN PATENT DOCUMENTS

WO    2006049787 A2    5/2006
WO    2012088201 A2    6/2012
(Continued)

OTHER PUBLICATIONS

International Searching Authority. International Search Report and Written Opinion for application PCT/US2021/051376. Mailed on Dec. 27, 2021. 17 pages.

(Continued)

*Primary Examiner* — Jonathan Cwern
(74) *Attorney, Agent, or Firm* — QUARLES & BRADY LLP

(57)                ABSTRACT

A system and method by which a catheter tube may be automatically driven to a target location within the body of a subject, such as an enteral cavity or respiratory tract of the subject. The catheter tube may include an imaging device, a transceiver, a spectrometer, and a battery embedded in a tube wall at a distal end of the catheter tube. The imaging device may capture image data of structures proximal to the distal end of the catheter tube. An articulated stylet may be inserted in the catheter tube, which may be controlled by a robotic control engine according to navigation data generated by an artificial intelligence (AI) model based on the topographical image data. The spectrometer may sample and identify biomarkers proximal to the catheter tube. A remote computer may implement the robotic control engine and AI model and may wirelessly receive the image data from the transceiver.

20 Claims, 21 Drawing Sheets

Related U.S. Application Data

(60) Provisional application No. 62/821,606, filed on Mar. 21, 2019.

(51) Int. Cl.
  *A61B 34/30* (2016.01)
  *A61B 90/00* (2016.01)
  *G06N 3/08* (2023.01)

(52) U.S. Cl.
  CPC .......... *A61B 5/0084* (2013.01); *A61B 5/6871* (2013.01); *A61B 5/6873* (2013.01); *A61B 34/20* (2016.02); *A61B 34/30* (2016.02); *G06N 3/08* (2013.01); *A61B 2090/373* (2016.02)

(56) References Cited

U.S. PATENT DOCUMENTS

| | | | |
|---|---|---|---|
| 2003/0028499 A1 | 2/2003 | Anderson et al. | |
| 2003/0214580 A1 | 11/2003 | Iddan | |
| 2006/0041199 A1* | 2/2006 | Elmaleh | A61B 5/02007 |
| | | | 600/478 |
| 2006/0147100 A1* | 7/2006 | Fitzpatrick | G06T 7/344 |
| | | | 382/154 |
| 2008/0253523 A1 | 10/2008 | Boyden et al. | |
| 2008/0275300 A1 | 11/2008 | Rothe et al. | |
| 2009/0171151 A1 | 7/2009 | Choset et al. | |
| 2010/0222747 A1 | 9/2010 | Wenchell et al. | |
| 2010/0305503 A1 | 12/2010 | Fang et al. | |
| 2012/0078055 A1 | 3/2012 | Berci et al. | |
| 2012/0136242 A1 | 5/2012 | Qi et al. | |
| 2012/0271170 A1 | 10/2012 | Emelianov et al. | |
| 2012/0302875 A1 | 11/2012 | Kohring | |
| 2013/0023774 A1 | 1/2013 | Crowley | |

| | | | |
|---|---|---|---|
| 2014/0005553 A1* | 1/2014 | Ryan | A61B 5/02007 |
| | | | 600/473 |
| 2014/0243660 A1* | 8/2014 | Klinder | A61B 5/742 |
| | | | 600/424 |
| 2016/0135776 A1* | 5/2016 | Chandler, Jr. | A61B 5/055 |
| | | | 600/411 |
| 2017/0296032 A1* | 10/2017 | Li | A61B 6/03 |
| 2018/0247153 A1* | 8/2018 | Ganapati | G06F 18/285 |
| 2018/0250484 A1 | 9/2018 | McCormick et al. | |
| 2018/0293737 A1* | 10/2018 | Sun | G06T 7/251 |
| 2018/0296281 A1* | 10/2018 | Yeung | A61B 34/32 |
| 2018/0360479 A1* | 12/2018 | Hofmann | A61B 34/20 |
| 2019/0046417 A1 | 2/2019 | Flexman et al. | |
| 2020/0250803 A1* | 8/2020 | Gu | G06V 10/25 |

FOREIGN PATENT DOCUMENTS

| | | |
|---|---|---|
| WO | 2013056006 A2 | 4/2013 |
| WO | 2018122837 A1 | 7/2018 |
| WO | 2018200063 A1 | 11/2018 |

OTHER PUBLICATIONS

International Searching Authority. International Search Report and Written Opinion for application PCT/US2020/023793. Mailed on Jun. 12, 2020. 10 pages.

CardinalHealth, Kangaroo(TM) Feeding Tube with IRIS Technology, Product Information, https://www.cardinalhealth.com/en/product-solutions/medical/enteral-feeding/kangaroo-feeding-tube-with-iris-technology.html, 2024, 2 pages.

Lombard, B. et al., Chapter 10, Robot-Assisted Endo- and Transnasal Surgery, in Robotics and Digital Guidance in ENT—H&N Surgery, 2017, pp. 157-176.

European Patent Office, Extended Search Report, Application No. 21870431.0, Aug. 30, 2024, 7 pages.

* cited by examiner

SIDE VIEW

400

422

424

416

426

414

500

504

502

502

504

500

502

511

506

600

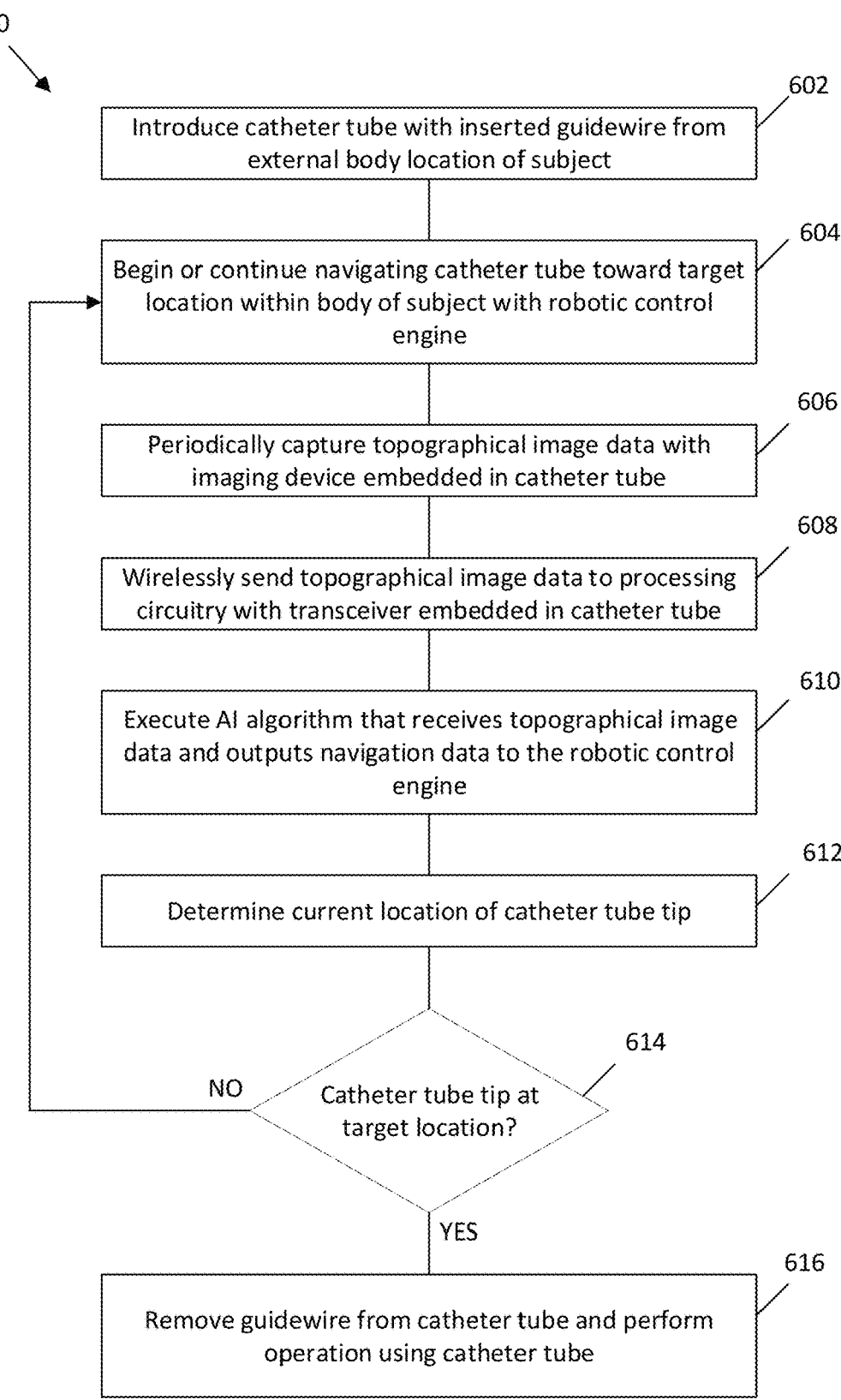

602

Introduce catheter tube with inserted guidewire from external body location of subject

604

Begin or continue navigating catheter tube toward target location within body of subject with robotic control engine

606

Periodically capture topographical image data with imaging device embedded in catheter tube

608

Wirelessly send topographical image data to processing circuitry with transceiver embedded in catheter tube

610

Execute AI algorithm that receives topographical image data and outputs navigation data to the robotic control engine

612

Determine current location of catheter tube tip

614

NO    Catheter tube tip at target location?

YES

616

Remove guidewire from catheter tube and perform operation using catheter tube

FIG. 6

Algorithm 1: Robot Guidance Algorithm

---

```
FUNCTION detect webcam(yolo): initialize tracker
    initialize parameters read a frame from input stream video vidFps <- get video fps, detFps <- desired detection
    frame rate while True:
        dRot <- 0, dBend <- 0
        read a frame from input stream video
        IF frame is present AND counter < int(vidFps/detFps) AND counter != 0: success, roi <- update tracker
            IF success AND counter < int(vidFps/detFps):
                isTracked <- True
                IF perimeter of bounding box > tk AND distance from lower center > tc:
                    draw bounding box into the frame isInproximity <- True ENDIF ELSE: pass
                    draw bounding box into the frame
                ENDIF
                IF horizontal center of bounding box <-(offset): dRot <--1
                    ENDIF
                ELSEIF horizontal center of bounding box > offset: dRot <- 1 ENDIF
                ENDIF counter += 1 dBend <- vertical distance from lower center IF counter % 5 = 4:
                    sock com(dRot, dBend, isTracked, isInproximity) ENDIF
            ELSEIF success AND counter = int(vidFps/detFps): isTracked <- False sock com(dRot, dBend, isTracked,
            isInproximity) counter <- 0, roi <- None, initialize tracker ENDIF ELSE:
                isTracked <- False sock com(dRot, dBend, isTracked, isInproximity) counter <- 0, roi <- None,
            initialize tracker ENDIF
        ENDIF ELSE:
            isTracked <- False
            dBend <- 0, dRot <- 0 counter <- 0 frame, bounding box, score <- yolo.detect image(frame)

IF (score > s1 AND hasTracked = False) or (score > s2 AND hasTracked = True): draw bounding box into the
                frame counter <- 1, initialize tracker
                IF isInproximity = True AND perimeter of bounding box > td AND score > sd:
                    isInproximity <- False ENDIF
            ENDIF ELSE:
                pass ENDIF counter += 1
            IF counter % 5 = 4:
                sock com(dRot, dBend, isTracked, isInproximity) counter <- 0 ENDIF
        ENDIF show frame ENDWHILE clean up
ENDFUNCTION
```

FIG. 14A

Algorithm 2: Robot Control Algorithm counter <-- 0 plunge counter <-- 0, rotate counter <-- 0, bend counter <-- 0

```
FUNCTION on soc(self, msg):
    auto linear vel <-- adjusting constant plunge auto angular vel <-- msg.data[0] * adjusting constant rotate auto
    pull vel <-- msg.data[1] * adjusting constant bend IF msg.data[3] == 1: OUTPUT "Auto Control Mode: INSERT"
        repeat interchanging rotation while plunging and straightening the bend log on each counter
        ENDIF                                                    c
    ELSEIF msg.data[2] == 0:
        IF msg.data[3] == 0:
            OUTPUT "Auto Control Mode: SEARCH" two interchanging rotation with and without bending while plunging
            log on each counter ENDIF
        ENDIF ELSEIF msg.data[2] == 1: OUTPUT "Auto Control Mode: TRACK" plunge auto linear vel, rotate auto angular
    vel, bend auto pull vel
        log on each counter ENDIF
    ENDIF
ENDFUNCTION
```

FIG. 14B

SEARCHING
- TRACK = FALSE
- ROTATE: PREDEFINED
SEARCHING MOTION COMPLEX (SMC)
- PLUNGE: SMC
- BEND: SMC

TRACKING
- TRACK = TRUE
- ROTATE: ACCORDING TO DETECTION
- PLUNGE: CONSTANT
- BEND: ACCORDING TO DETECTION

BOUNDING BOX SIZE

INSERTING
- TRACK = FALSE
- ROTATE: PREDEFINED
INSERTING MOTION COMPLEX (IMC)
- PLUNGE: IMC
- BEND: IMC

ROBOTIC ARTIFICIAL INTELLIGENCE NASAL/ORAL/RECTAL ENTERIC TUBE

CROSS-REFERENCE TO RELATED APPLICATIONS

This application is based on, claims the benefit of, and claims priority to U.S. Provisional Application No. 62/821, 606, filed Mar. 21, 2019, and to International Application PCT/US20/23793, filed Mar. 20, 2020, each of which is hereby incorporated herein by reference in its entirety for all purposes.

STATEMENT OF FEDERALLY SPONSORED RESEARCH OR DEVELOPMENT

The invention was made without any government support, partnership or grant.

BACKGROUND OF THE INVENTION

This invention relates to methods and systems for placing a tube from an external surface of the body (e.g., nasal/oral/ rectal) cavity into the enteral space anywhere from the stomach to the small or large intestine or the other body lumens and orifices, including the respiratory tract.

During the course of medical care, the need to access the enteral system is extremely common. For example, access to the enteral system may be needed to remove gastric or intestinal compounds, to introduce material into the enteral system or to obtain images or samples. Examples of removing gastric or intestinal compounds include gastric or intestinal decompression in the setting of gastric or intestinal paralysis, or in the setting of ingestion of toxic compounds. Examples of the need for introduction of material, which are more common, include feeding or providing medications to patients incapable of completing these activities independently. The need for imaging is common in both the upper and lower intestinal tract to observe and obtain samples from these areas. This includes the use of diagnostic esophago-gastro-duodenoscopy, and colonoscopy. This is generally accomplished through the manual placement of a nasogastric tube (NGT) or an orogastric tube (OGT), a rectal tube, or an endoscope for either the upper or lower intestinal tract. Accessing the enteric system can be accomplished rostrally or caudally.

A rostral approach to accessing the enteric system involves naso/oral access. The rostral approach will now be described.

The manual placement of naso/oral enteric tubes is a common procedure in the hospital setting and is crucial in treating patients with compromised oral intake. These manual placements are performed in multiple hospital settings, including the emergency room, the inpatient setting, and occasionally even in the outpatient setting. The use of these tubes is particularly common in the Intensive Care Unit (ICU) setting. It is estimated that over 1.2 million of these devices are placed annually in the United States alone. Although this procedure is performed frequently and considered generally to be simple, it does require a clinician with subject matter expertise to assist in the accurate manual placement of the device. Depending on institutional policy, the procedure may only be performed by a physician or a nurse with specialized skills.

The main concerns with the current model of naso/oral enteric tube placement are two-fold: (1) the safety of this placement for patients, and (2) the efficiency of the placement process.

Despite the presumed simplicity of the procedure for placing naso/oral enteric tubes, it is known to be a source of frequent and sometimes fatal complications. The worst of these complications come from the inadvertent placement of the tube into the respiratory tract with the potential complication including the introduction of feeding material into the lung, pneumonias, lung rupture with consequent pneumothorax and bronchopleural fistulas. All these complications can be fatal. The reason for these complications is that over 70% of naso/oral enteric tubes are manually placed blindly through the nose or mouth, traveling through the esophagus into the stomach or intestines. This blind placement is performed without any visual guidance, and many times results in erroneous tube placement and the resultant complications. In a minority of cases, these tubes are placed by highly specialized physicians, who are trained and equipped to use endoscopic or radiologic techniques to assist in the correct placement. However, involvement of such specialists is resource-intensive and creates a significant delay in accessing the enteral system of the patient. As a result, it is not ideal for either the healthcare system or the patient to utilize such resources for the placement of these devices.

In addition, there is often considerable discomfort for the patient associated with the placement of a naso/oral enteric tube. The inflexibility of the tube in conventional systems leads to difficulty navigating the complex pathway from the nose/mouth to the enteric system. As a result, the tube will often contact the patient's throat with some force, which can result in discomfort or injury.

Beyond the safety concerns of this procedure, the process of placing naso/oral enteric tubes tends to be inefficient. In a typical setting, the tube is manually placed blindly at the bedside by a clinician. Because of the potentially fatal complication of inserting the tube into the lung, the position of the tube in either the stomach or the intestine must be confirmed by radiology. For example, after the placement of a naso/oral enteric tube, a radiographic scan of the chest and abdomen must be obtained so that a trained radiologist or physician can confirm that the naso/oral enteric tube has been placed correctly. The need for this confirmation introduces a significant delay as radiographic scans are not always readily available. Once the radiographic scan has been performed, the scan must be reviewed by a radiologist or physician to verify correct distal tube placement before the tube can be utilized clinically. If the radiographic scan reveals that the tube is in the incorrect position, or if the position is not completely discernible, then the process must be repeated with a re-positioning of the tube and a repeat a radiographic scan. With this multi-step process, the patient's clinical needs for either enteral decompression, medication delivery, or initiation of feedings can be significantly delayed, on occasions up to 24 hours after the initiation of the process.

The use of such confirmatory resources, including radiology technicians and clinicians, bedside clinicians, radiographic imaging, and potentially additional naso/oral enteric tubes, can add considerable cost to this procedure, beyond the treatment delays it incurs.

The use of radiographic imaging introduces additional ionizing radiation to the patient, which is associated with known risks. Exposure to radiation causes damage to cells, tissues, and organs, which can lead to cancer and other medical problems. Efforts are underway across the healthcare industry to reduce exposure to radiation wherever possible, in order to protect patients from unnecessary risk. Specific populations are at increased risk of harm due to radiation, such as pediatric patients, patients who have undergone radiation therapy, patients who have been exposed to radiation from a nuclear accident, and people who live at high altitude.

While naso/oral enteric tubes with visual guidance exist that allow specialized clinicians to see the trajectory of the tubes, these devices require the specialized knowledge of the clinician, who in placing the device must be capable of discerning from captured images when the ideal position of the tube is reached. In institutions that have clinicians with this expertise, there will be a delay imposed by the avail-ability of such experts. In institutions with no such expertise, this solution becomes non-operative. Furthermore, even with visual guidance, human mistakes in interpretations of the visual images and failed placement may still occur. It is widely understood that these tubes can be misplaced in error even when visual guidance is provided.

Furthermore, given the inevitability of tube migration within the enteric system and the need for maintaining proper positioning of the naso/oral enteric tube over a period, continued monitoring by an expert clinician is required. Conventional methods of naso/oral enteric tube placement rely on repeat radiographic scans to confirm tube placement periodically. Exposure to damaging radiation associated with radiographic imaging is increased with each additional scan obtained. The risk of damage due to feeding or delivering medications to the incorrect enteric location are increased when there is no indwelling localization mechanism associated with the naso/oral enteric tube.

Thus, an efficient and safe form of naso/oral enteric tube placement is needed.

Complex placement often requires the involvement of specialized endoscopes and endoscopically trained physi-cians for placement. This delays placement and given the enhanced complexity of the system, implies greater risk to the patients. Therefore, a safer, less complex, and automated way of guiding and imaging the upper intestinal tract is required. This will also allow for the automated system to obtain images and samples of the enteral system.

A caudal approach to accessing the enteric system involves rectal access. The caudal approach will now be described.

Similar to the issues with accessing the upper intestinal tract, placement of an enteral tube through the rectum is a blind and manual procedure. This has the potential compli-cation of causing damage to the lower intestinal tract and misplacement. A safe, simple, automated system for place-ment of an enteral tube through the rectum into the lower intestinal tract is required that would allow for infusion of material, decompression of the large bowel, and acquisition of images and samples through an automated system not requiring specialized personnel to perform.

The main concerns with the conventional methods of rectal enteric tube placement are two-fold: (1) the safety of this placement for patients, and (2) the efficiency of the placement process.

As mentioned, the placement of rectal tubes for the purpose of large bowel decompression is performed manu-ally and with no guidance. In other words this is performed as a blind procedure with the risk inherent in the unguided introduction of any device including creation of bleeding, intestinal rupture or misplacement This becomes even more severe if the placement of this tube is then followed by introduction of material such as those intended to facilitate intestinal decompression.

If the goal of tube placement is for obtaining images and tissue samples, the problem is a different and more signifi-cant. In this case, the need for direct vision by a specialized physician such as a gastroenterologist necessitates the exis-tence of highly specialized personnel and equipment. In this case, there exists the need for gastroenterologists capable of using an endoscopic device designed for use in the rectum and entire large bowel. The complexity of both the expert personnel and the equipment required to perform the pro-cedure creates two major problems for the delivery of adequate patient care.

The first problem is patient access. Given the nature of expert personnel and equipment availability through the world, the access to needed diagnostic imaging capable of discerning lesions from within the enteral system is extremely limited. The recommendation for diagnostic colo-noscopy for all patients above a certain age is severely constrained by the availability of these resources.

The second problem is that it is a complex procedure with significant patient discomfort and risk. The need for a physician to be able to visualize the entire colon in real time requires the use of large endoscopes developed for the exploration of the colon. This requires a full hospital pro-cedure done under sedation/anesthesia in order to avoid patient discomfort. This is a combination of the fact that the equipment required is by necessity large and that the pro-cedure can be prolonged. This combination creates the need for a full operative and anesthetic intervention with its significant increased costs and, importantly, with increased patient risk both from the procedure and the anesthetic.

These are not only dangerous, uncomfortable, costly and inefficient processes, they also limit needed care. A system that improves upon these common problems would provide value and benefit to patients, clinicians, and healthcare systems.

SUMMARY OF THE INVENTION

Another type of tube placement that poses difficulty in the medical setting involves access to the respiratory tract. The need to enter the respiratory tract, specifically, the lungs, is often in an emergent situation where need to control the patient's breathing is paramount. In these situations, the failure to gain access to the lungs traversing though the body's natural pathways represented by the oral/nasal space, pharynx, glottis, and into the trachea can be fatal. Estab-lishing access to the trachea and lungs allows for a patient to be ventilated and oxygenated.

The respiratory tract approach will now be described.

Similar to the issues with accessing the enteric system, placement of an endotracheal intubation tube for respiratory tract access is a complex manual procedure. This has the potential complication of causing damage to the lips, teeth, oral cavity, epiglottis, larynx, or trachea, in addition to the issue of misplacement or failed placement. In either of these latter two scenarios of misplaced or failed placements, the urgent need to ventilate and oxygenate a patient remain unresolved. A safe, simple automated system for placement of an endotracheal intubation tube through the oropharynx into the trachea is required which would allow for ventila-tion, oxygenation, airway management, and respiratory sup-port. Currently this is done through a manual procedure, performed by highly skilled and trained individual. Pro-posed herein are solutions which utilize the automated system described in this document for accessing the enteric system and which would not require medical personnel to perform.

The need for such an automated intubation system is particularly valuable when a patient is encountered outside of standard hospital settings, specifically, in the field where first responders and medics often encounter traumatically injured patients. In the setting of trauma, the most important concern is always patient safety. Often patients have lost all control of basic physiologic functions, most important of which are maintenance of a functional airway, the ability to breathe and the need to maintain adequate circulation. These three are immortalized in the ABC's of care—Airway, Breathing and Circulation. Traumatic injuries are often accompanied by a loss of a viable airway and with it, the ability for a patient to continue providing oxygen to at risk tissues—making establishing a viable airway critical.

The development of a compact, portable, fully autonomous robotic device capable of providing an emergency airway to all our trauma patients will have a significant impact on the level of recovery and survival of these patients. This can be accomplished using visual based data and advanced data analytics and artificial intelligence to drive the device that allows for early, safe and dependable endotracheal intubation. Outcomes in trauma are determined by decision and actions made in the first 30-60 minutes of care and delivering advanced assistance to care givers as rapidly as possible at the point of care will improve outcomes for patients involved in such situations.

Currently only a minority of both civilian or military first medical responders are capable of advanced airway control by securing an airway with endotracheal intubation. This is a significant problem especially in patients suffering cardio-respiratory arrest, traumatic brain injury or facial, neck or chest wounds. Studies have demonstrated high levels of complications when advanced airways are attempted in non-hospital settings, such that this is not a skill that is required for Emergency Medical Technician certification. It is however critical to provide an adequate airway to all of these patients in the first hour of their injury or cardio-pulmonary failure, what is known as the "golden hour" because of the critical role determined by decision and actions made in the first 30-60 minutes of care. Delivering advanced assistance to care givers as rapidly as possible at the point of care will improve outcomes for patients involved in such situations.

The main concerns with the conventional methods of endotracheal intubation tube placement are three-fold: (1) the safety of this placement for patients, (2) access to care based on the complexity and the efficiency of the placement process, and (3) risk to medical personnel:

1) Patient Safety: The placement of endotracheal tubes for the purpose of airway management and respiratory support is performed manually and with visual guidance through the use of various devices including a direct laryngoscope or video laryngoscopy. On occasion these tubes can be placed blindly using nasal endotracheal intubations. In any of these approaches, visualization is limited to varying extents leading to the risks inherent in the unguided introduction of any device including bleeding, tissue rupture, and, importantly, misplacement or even failed placement. Given these difficulties it is not uncommon to see prolonged intubation attempts during which the patient is subjected to life-threatening periods of lack of pulmonary ventilation and tissue oxygenation.

2) Access to Care. The complexity of the procedure and the associated risks necessitate that a highly trained and specialized clinical team be present to perform the intervention. The need for a sophisticated team of medical personnel for tracheal access and securing of an airway is particularly problematic, especially since the setting in which this is required are often emergent and life threatening. Inability to resolve respiratory failure in this setting by effectively intubating a patient can be fatal. This is a special concern with patient in a non-clinical setting such as a patient's home, the battle field, or an emergency transport vehicle. This lack of patient access to this life saving procedure is one of the major problems with the current system of endotracheal intubation.

3. Risk to medical personnel. During endotracheal intubation tube placement, given the nature of the placement access point in the oral/nasal and pharyngeal cavities, the patient is likely to release airborne droplets. This process, known as aerosolization, is considered the point during which all healthcare person now in the immediate vicinity of the procedure are the highest lists risk of contagion with any pathogen that the patient may have. Given the fact that respiratory failure often is associated with infectious causes such as viral or bacterial pneumonias, this is a critical safety risk for healthcare personnel involved with the procedure of intubation. Limiting exposure to infection transmission is critical in all settings, but particularly so in the setting of a respiratory pandemic such as COVID-19 infectious transmission. To protect the medical personnel involved in the procedure from this infectious transmission, personal protective equipment (PPE) is employed. However the considerable size of the medical team needed for this blinded, manual endotracheal intubation puts a number of medical personnel at risk of infection. This risk exists when treating all hospitalized patients, but is especially great during a global pandemic of a respiratory illness such as what the world is currently experiencing with COVID-19.

Manual endotracheal intubation is not only a dangerous, uncomfortable, costly, and inefficient process, it also puts medical personnel at risk of airborne infectious transmission.

Thus there is a need for an automated endotracheal intubation solution that would limit the exposure of medical personnel to such risk of infection.

Systems and methods for the automated placement of a catheter tube at a target location within the body of a subject are disclosed. For example, a catheter tube may be automatically navigated and driven into the enteral space, from either a rostral approach from the nasal/oral cavity, from a caudal approach from the rectum, or from the oral cavity to the respiratory tract. This automatic navigation may be performed using a robotic mechanical device guided by artificial intelligence models to create a "self-navigating" catheter. A system performing such placement may not require the intervention of a clinician and therefore may eliminate the need for specific expertise for the positioning or placement of the device into the enteral system or respiratory tract of a subject (e.g., patient).

The system may therefore enable directed placement and immediate confirmation of correct positioning of the tube using topographic imaging data captured by one or more image sensors of the system and corresponding to the cavity in which the tube is positioned. The embodiments described herein may be applied for naso- and oro-enteric tube placements, rectal enteric tube placements as well as the placement of percutaneous feeding tubes, and placement of endotracheal intubation tubes. It should be understood, however, that the described embodiments are intended to be illustrative and not limiting. For example, embodiments described herein are not limited in any way to a particular port of entry to access the enteral system or respiratory tract, or to the final position of the tube itself.

This system will also make possible the acquisition of imaging data and/or samples from within the cavity. It should be understood that imaging data described herein may refer to imaging data acquired through one or more (e.g., multimodal) sources and/or acquired using one or more imaging techniques, examples of which will be described below.

The system may employ artificial intelligence models for processing the data input from the imaging sensors, which may enable both "self-navigating" catheter placement as well as subsequent enteral or respiratory environment calculations.

The system may furthermore remain indwelling in the patient as clinically indicated. In this way, the data obtained from the sensors in the distal catheter may be utilized by the clinical team for continuous monitoring of the enteral or respiratory environment. This monitoring may include catheter localization information and, in the enteric system, biomarkers and pH metrics, and enteric volume measures.

The embodiments described herein may be applied for naso- and oro-enteric percutaneous feeding tubes as well as the placement of rectal tubes, respiratory tract access via endotracheal intubation, and their subsequent monitoring, imaging and sampling capabilities. It should be understood, however, that the described embodiments are intended to be illustrative and not limiting. For example, embodiments described herein are not limited in any way to a particular port of entry to access the enteral system or respiratory tract, or to the final position of the tube itself.

In an example embodiment, a system may include a catheter tube that includes a tube wall that defines a lumen, an imaging device configured to capture image data, the imaging device disposed at a distal end of the catheter tube, a transceiver coupled to the imaging device and configured to wirelessly transmit the captured image data, the transceiver disposed at the distal end of the catheter tube, an articulated stylet disposed in the lumen of the catheter tube, the articulated stylet comprising an articulated distal end, a robotic control and display center. The robotic control display center may include wireless communication circuitry that communicates with and receives the image data from the transceiver, processing circuitry configured to execute an artificial intelligence algorithm that analyzes the image data and outputs corresponding navigation data, and a robotic control engine that drives the articulated stylet toward a target destination inside a body of a subject based on the navigation data.

In some embodiments, the imaging device may be a topographic imaging device, and the captured image data may include topographic image data.

In some embodiments, the imaging device may be a visual imaging device, and the captured image data may include still imaging data or visual image video data.

In some embodiments, the imaging device and the transceiver may be embedded in the articulating stylet. The articulated stylet may also include an insufflating channel embedded in the articulated stylet and a light source embedded in the articulated stylet.

In some embodiments, the imaging device and the transceiver may be embedded in the tube wall of the catheter tube. The catheter tube may further include an insufflating channel embedded in the tube wall of the catheter tube. The catheter tube may further include a light source embedded in the tube wall of the catheter tube.

In some embodiments, the imaging device may include a time-of-flight imaging device, the captured imaging data may include time-of-flight imaging data, and the time-of-flight imaging device may be configured to capture the time-of-flight image data using multiple wavelengths of light.

In some embodiments, the processing circuitry may be configured to execute a volume sensing module configured to obtain volume measurements of an enteral space, respiratory tract, or other cavity in which the catheter tube is disposed based on time of flight imaging using multiple wavelengths of light. The volume sensing module may, based on the volume measurements, determine a first volume value corresponding to a total volume of the enteral space, a second volume value corresponding to a first portion of the total volume that is empty, and a third volume value corresponding to a second portion of the total volume that is filled with material. The third volume may be calculated by subtracting the second volume from the first volume.

In some embodiments, the robotic control engine may be configured to drive the articulated stylet by controlling at least one articulation of the articulated stylet to control a direction of movement of the articulated stylet, the articulated stylet having at a minimum three degrees of freedom including plunge, rotation, and tip deflection.

In some embodiments, the catheter tube may further include a stylet spectrometer and a stylet transceiver disposed at the distal end of the articulating stylet. The stylet spectrometer may be configured to sample and analyze substances at the distal end of the articulating stylet to produce stylet spectrometer data and the stylet transceiver may be configured to wirelessly transmit the stylet spectrometer data to the robotic control and display center.

In some embodiments, the catheter tube may further include a spectrometer disposed in the distal end of the catheter tube, the spectrometer being configured to collect and analyze samples to produce spectrometer data.

In some embodiments, the robotic control and display center may include a display device. The transceiver may be configured to send the spectrometer data to the processing circuitry via the wireless communication circuitry. The processing circuitry may be configured to analyze the spectrometer data to identify a biomarker to which the sample corresponds. The display device may be configured to display information related to a location and a status of the catheter tube and information related to the biomarker.

In some embodiments, the at least one artificial intelligence model may include a detection and tracking model that processes the captured image data in near-real time, a deep-learning detector configured to identify orifices and structures within the enteral cavity or respiratory tract, the deep-learning detector including at least one convolutional-neural-network-based detection algorithm that is trained to learn unified hierarchical representations, that identifies the orifices and structures based on the captured image data, and that calculates the navigation data based on the captured image data and the target destination, and a median-flow filtering based visual tracking module configured to predict the motion vector of the articulated stylet using sparse optical flow.

In an example embodiment, a robotic control and display center may include wireless communication circuitry that communicates with and receives topographical image data from a transceiver of a catheter tube, processing circuitry configured to execute an artificial intelligence model that analyzes the topographical image data and a target destination and outputs corresponding navigation data, and a robotic control engine that automatically drives an articulated stylet disposed inside the catheter tube toward the target destination inside a body of a subject based on the navigation data.

In some embodiments, the robotic control engine may be configured to control a direction of movement of the articulated stylet by controlling an articulation in a distal end of the articulated stylet.

In some embodiments, the robotic control engine may be configured to control a direction of movement of the articulated stylet by modifying a rotational position of the articulated stylet.

In some embodiments, the wireless communication circuitry may be configured to receive spectrometer data from the transceiver, the spectrometer data corresponding to a substance sampled by a spectrometer of the catheter tube. The processing circuitry may be configured to execute an additional artificial intelligence model that receives the spectrometer data and outputs an identity of a biomarker to which the substance corresponds.

In some embodiments, the robotic control and display center may further include a display device that is configured to display information related to a location and status of the catheter tube and the identity of the biomarker.

In some embodiments, the robotic control engine may be configured to drive the articulated stylet without receiving manual guidance.

In an example embodiment, a catheter assembly may include a catheter tube and an articulated stylet. The catheter tube may include a tube wall that defines a lumen, an imaging device configured to capture image data, the imaging device disposed at a distal end of the catheter tube, and a transceiver coupled to the imaging device and configured to wirelessly transmit the captured image data to a remote computer system, the transceiver being disposed at the distal end of the catheter tube. The articulated stylet may be disposed in the lumen, and may be configured to be automatically driven to a target location within a subject based on at least the captured image data.

In some embodiments, the articulated stylet may include an articulation, the articulation being configured to bend to control a direction of motion of the articulated stylet while the articulated stylet is being automatically driven to the target destination.

In some embodiments, the articulation of the articulated stylet may possess at least three degrees of freedom comprising plunge, rotation, and tip deflection.

In some embodiments, the catheter tube may further include a spectrometer disposed at the distal end of the catheter tube, the spectrometer being configured to sample and analyze substances proximal to the distal end of the catheter tube to produce spectrometer data. The transceiver may be configured to wirelessly transmit the spectrometer data to the remote computer system.

In some embodiments, the imaging device, the spectrometer, and the transceiver may each be embedded at different locations in the tube wall of the catheter tube. The catheter tube may further include an insufflation channel embedded in the tube wall.

In some embodiments, the image data may include topographical image data depicting structures proximal to the imaging device.

BRIEF DESCRIPTION OF THE DRAWINGS

FIG. 5B illustrates a range of motion of the articulated stylet.

FIG. 6 illustrates a process flow for an exemplary method of automatically driving a catheter tube to a target destination using navigation data derived by one or more artificial intelligence models from image data generated by an imaging device disposed at a distal end of the catheter tube.

FIG. 14A provides an example of a robot guidance algorithm and FIG. 14B provides an example of a robot control algorithm.

DETAILED DESCRIPTION

Figure 1A:
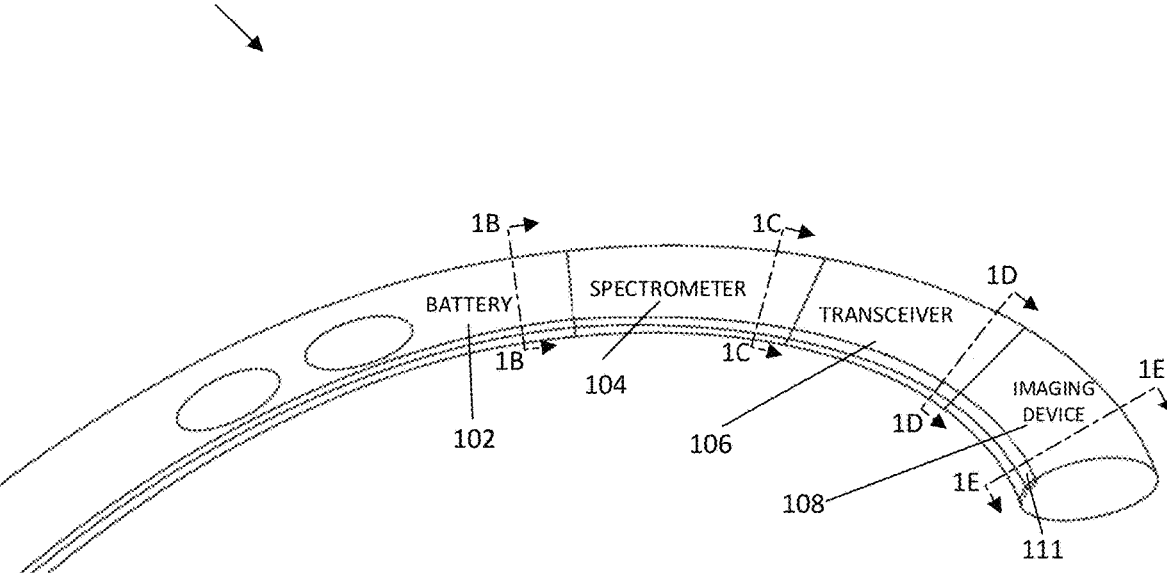
FIGS. 1A through 1E illustrate an exemplary catheter tube that includes a battery, a spectrometer, a transceiver, and an imaging device, and a channel that may or may not be used for insufflation of the gastro-intestinal tract during placement of the device.

Systems and methods disclosed herein relate to automated placement of a catheter tube at a target location within the body of a subject (e.g., into the subject's enteral system via the subject's nose, mouth, or rectum, into the respiratory tract via the nasal or oral cavity, or via a surgical incision that extends to the subject's stomach or intestine directly). The catheter tube may further include a channel that may or may not be used for insufflation of the gastro-intestinal tract or respiratory tract during placement of the device. The catheter tube may include an imaging device, which can be a topographical imaging device that captures topographical images of structures in the vicinity of the distal end (e.g., tip) of the catheter tube, and/or a visual imaging device that captures pictures or videos from within the enteral cavity. Imaging data generated by such imaging devices may be topographical image data, still image data, video data, or a combination of some or all of these. The catheter tube may further include an image guide and light guides that can connect to a camera or spectrometer that is disposed outside the subject, which may be used to perform optical analysis of enteral spaces or respiratory tract of the subject. The catheter tube may further include a spectrometer, which may analyze biomarkers or other chemicals in the vicinity of the distal end of the catheter tube (e.g., such as biomarkers in tissue around the tip of the catheter tube). The catheter tube may further include a transceiver, which may wirelessly transmit and receive data to and from a remote device. The transceiver and wireless communication circuitry of the remote device may communicate using a wireless personal area network (WPAN) according to a short-wavelength UHF wireless technology standard, such as Bluetooth®, for example. It should be understood that other WPAN standards, such as ZigBee®, may instead be used in some embodiments. The remote device that communicates with the transceiver of the catheter tube may be a Robotic Control and Display Center (RCDC), which may include a display, an articulated stylet, a robotic control engine, processing circuitry, and wireless communication circuitry. The articulated stylet may be an articulated robotic navigating articulated stylet dimensioned to be placed within the catheter tube. The robotic control engine may drive the articulated stylet and may control its direction, so that the articulated stylet, and therefore the catheter tube, may automatically navigated through an opening in a subject's body (e.g., the nose or mouth of the subject) to a target location within the subject's body. One or more artificial intelligence (AI) models may be implemented by the processing circuitry of the RCDC. The AI model (s) may include one or more trained machine learning neural networks, which operate on image data received from the imaging device of the catheter tube via the transceiver to determine the direction in which the robotic control engine will drive the articulated stylet and catheter tube. The display may be a digital display screen, and may display information regarding the placement of the distal end of the catheter tube in the subject's body, continuously updated status information for the catheter tube, and biomarker information collected by the spectrometer of the catheter tube.

An artificial intelligence based detection and tracking model may be executed to enable the RCDC to traverse autonomously, and may use real-time captured enteral images (e.g., represented via topographic image data, still image data, and/or video data) or other sensor data, which may be captured by one or more imaging devices disposed at a distal end of an articulated stylet/catheter tube. The objective may be to first detect the nasal/oral/rectal opening from the enteral or respiratory tract images and then follow a path predicted by a detection-tracking based mechanism. For detection, a deep-learning YOLO-based detector may be used to detect the nasal/oral/rectal orifice, environmental features, and structures within the enteral cavity or respiratory tract. For example, the deep-learning YOLO-based detector may further distinguish between a nasal/oral/rectal orifice and visually similar nearby structures. For example, once inside the enteral cavity or respiratory tract, the deep-learning YOLO-based detector may subsequently discriminate between visually similar structures over the course of the path to the enteral or tracheal target. For tracking, a fast and computationally efficient median filtering technique may be used (e.g., at least in part to predict the motion vector for the articulated stylus in order to navigate the articulated stylus to a target destination).

For detection of orifices, structures, and surrounding environment, a convolutional neural network (CNN) based detector may be used in conjunction with the deep-learning YOLO-based detector (e.g., which may be collectively referred to as a "deep-learning detector"), as it has achieved a state-of-the-art performance for real-time detection tasks. Different from traditional methods of pre-defined feature extraction coupled with a classifier, these CNN-based detection algorithms may be designed by a unified hierarchical representation of the objects that are learned using imaging data. These hierarchical feature representations may be achieved by the chained convolutional layers which transform input vector into a high dimensional feature space. For enteral or tracheal detection, a 26-layer or greater CNN based detection model may be employed. In such a model, the first 24 layers may be fully convolutional layer that are pre-trained on Imagenet dataset, and the final two layers may be fully connected layers which output the detected regions. The algorithm may further be fine-tuned with colored images of the enteric regions.

For tracking, a median-flow filtering based visual tracking technique (e.g., performed by a median-flow filtering based visual tracking module) to predict the motion vector for the robotic placement device may be employed. The median flow algorithm may estimate the location of an object with sparse optical flow, and the tracking based system may be based on the assumption that an object consists of small and rigidly connected blocks or parts which more synchronously together with motion of the whole object. In some embodiments, the object may be the nasal orifice, oral orifice, rectal orifice, or structures within the enteric cavity or respiratory tract. Initialization of the algorithm may be performed by setting up a bounding box in which the enteral/tracheal cavity is located at first, and within this region of interest a sparse grid of points may be generated. The motion of the enteral/tracheal cavity detected by optical flow in the captured images may be computed as the median value of differences between coordinates of respective points that are located in the current and preceding images. Only those points which have been regarded as reliable during the filtering may be taken into account. The algorithm may be capable of estimating the object scale variations.

For implementation, the object detection may be accomplished via YOLO-based algorithm and object tracking may be accomplished via median flow tracker (e.g., which may be implemented through Python). The environment may be built on Ubuntu, for example. The graphics processing unit (GPU) integration cuDNN and CUDA toolkit may be used to implement these algorithms/models.

The training segment may be implemented by supplying annotated images to a Keras implementation of YOLO. The Keras and TensorFlow backend may be used. The dataset may be created with annotated software VoTT (Microsoft, Redmond, WA), with an adopted learning rate of 103 for 1,000 training epochs and saved model parameters every 100 epochs. Among the saved models, the one that achieves the highest Average Precision (AP) for Intersection over Union (IoU) of 50% or higher considered as positive on the validation set may be selected as the final model to be evaluated on the training set.

The detection segment may again be implemented based on Keras running TensorFlow on the backend. For tracking, the tracking API in OpenCV may be used. The bounding box may be detected by YOLO and passed to Median Flow tracker at m:n ratio, in order to realize real-time detection and tracking.

FIGS. 1A-1E show the distal end of an illustrative catheter tube 100, which may include a battery 102, a spectrometer 104, a transceiver 106, a channel 111 that may or may not be used for insufflation of the gastro-intestinal tract during placement of the device, and an imaging device 108. While the example of FIGS. 1A-1E is provided in the context of components being are embedded a tube wall of the catheter tube 100, it should be understood that any of the battery 102, the spectrometer 104, the transceiver 106, and/or the imaging device 108 (collectively referred to here as "embedded components") may additionally or alternatively be included in (e.g., embedded in a wall of) an articulated stylet (e.g., articulated stylet 420, 502, of FIGS. 4A, 4B, 5A-C) that may be inserted into a catheter tube such as the catheter tube 100, such that when the articulated stylet is fully inserted into the catheter tube the embedded components will be located at a distal end of the catheter tube.

As shown in FIG. 1A, the imaging device 108 may be positioned at the distal end of the catheter tube 100 closest to the tip, followed in order by the transceiver 106, the spectrometer 104, and the battery 102. The catheter tube 106 may be a hollow, substantially cylindrical tube made of polyurethane or silicone, for example. The catheter tube 100 may, for example, be formed from Pebax (or other polymers). In some embodiments, the catheter tube 100 may be a multilayer catheter that includes an inner liner (e.g., laser cure stainless steel, polyimide, FEP or PTFE), a jacket (e.g., Pebax, possibly of multiple durometers), and, optionally, a stainless steel braid or coil or both, depending on pushability, "steerability', or flexibility requirements. The channel 111 may be coupled to a pump (e.g., an air or carbon dioxide pump), which may be housed in a remote device (e.g., the RCDC of FIGS. 4A, 4B). Air or other gases may be passed through the channel 111 by the pump to an opening in the end of the catheter tube 100 in order to perform insufflation of the gastro-intestinal tract of a subject, for example.

Figure 1B:
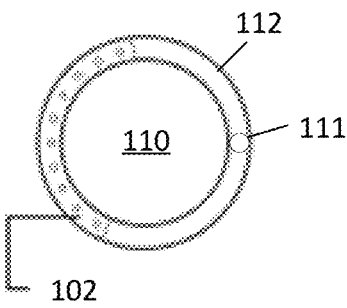

As shown in the cross-sectional view of FIG. 1B, the battery 102 may be partially or completely embedded in or attached to a tube wall 112 of the catheter tube 100. The battery 102 may provide electric power to the spectrometer 104, the transceiver 106, and the imaging device 108. In some embodiments, the battery 102 may be located in the lumen 110 of the catheter tube 100. For example, the battery 102 may be a lithium ion battery. As used herein a "lumen" refers to the central cavity of a catheter tube, with the lumen 110 referring to the central cavity of the catheter tube 100. As shown, the channel 111 may be embedded in the tube wall 112.

Figure 1C:
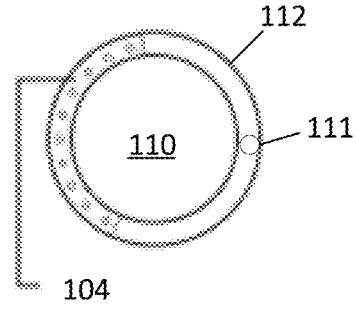

As shown in the cross-sectional view of FIG. 1C, the spectrometer 104 may be partially or completely embedded in or attached to a tube wall 112 of the catheter tube 100. In some alternate embodiments, the spectrometer may instead be disposed outside of the catheter tube 100, and connected to the distal end of the catheter tube 100 via an optical guide such as an optical fiber or bundle that is disposed in the lumen 110. The spectrometer may continuously analyze substances (e.g., biomarkers, such as those produced by organs of the human body) in the vicinity of the distal end of the catheter tube 100. For example, the spectrometer 104 may perform this analysis without directly interacting with sample substances being tested, instead leveraging the properties of light to perform spectral analysis. The results of an analysis performed by the spectrometer 104 may produce specific results related to biomarkers that may be included in a target organ, such as ion concentration, acidity, hormone levels, and toxicology analysis.

Figure 1D:
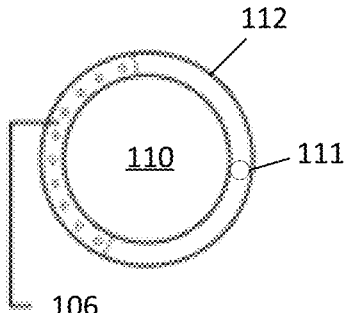

As shown in the cross-sectional view of FIG. 1D, the transceiver 106 may be partially or completely embedded in or attached to a tube wall 112 of the catheter tube 100. For example, the transceiver 106 may be a wireless personal area network (WPAN) transceiver that is configured to transmit and receive data wirelessly according to a WPAN protocol (e.g., Bluetooth® or Zigbee®). The transceiver 106 may wirelessly transmit data to a remote device (e.g., the RCDC device 400 of FIGS. 4A, 4B) for analysis. For example, data transmitted by the transceiver 106 may include a state of the distal end of the catheter tube 100 (e.g., position within an organ, proximity to surrounding structures), a state of an organ in which the catheter tube is located (e.g., volume of fluids, biomarker status, etc.). The transceiver 106 may also wirelessly transmit imaging data (e.g., topographic image data, still image data, and/or video data) captured by the imaging device 108 to the remote device. The transceiver 106 may transmit this data to the remote device both during the device placement process (e.g., as the catheter tube 100 is automatically driven to a target location), and during a continuous monitoring phase that may occur once the catheter tube 100 has reached the target location. In some embodiments, the transceiver 106 may only send data to the remote device without receiving instructions from the remote device. In other embodiments, the transceiver 106, in addition to receiving data to the remote device, may receive instructions from the remote device, such as instructions that, when executed, cause the devices in the catheter tip, such as the spectrometer 104, to perform specific functions (e.g., carrying out specific tests in the example of the spectrometer 104).

Figure 1E:
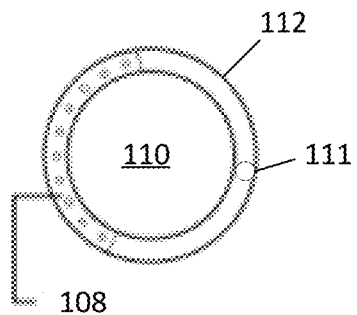

As shown in the cross-sectional view of FIG. 1E, the imaging device 108 may be partially or completely embedded in or attached to a tube wall 112 of the catheter tube 100. The imaging device 108 may include one or more image sensors, which may be, for example, topographic image sensors and/or visual image sensors. The imaging device 108 may capture image data ("captured image data") corresponding to structures (e.g., of the organ being traversed by the catheter tube 100) surrounding the distal end of the catheter tube 100. For example, LiDAR, time of flight imaging, visual image sensing (e.g., which may involve the capture of still images and/or video), or other applicable imaging techniques may be applied to capture the image data. Topographic image data that may be included in the captured image data may provide information related to the shape, volume, consistency, and location of the organ, or the portion of the organ, through which the distal end of the catheter tube 100 is traversing. The captured image data may be transmitted to and used by one or more artificial intelligence (AI) models executed by the remote device that is in wireless electronic communication with the transceiver 106, providing feedback to the AI model(s) regarding the location and position of the catheter tube 100 in the subject's body (e.g., in an organ thereof). Thus, the image data generated by the imaging device 108 may be used to guide the placement of the catheter tube 100 and to continuously monitor the location of the catheter tube 100 once it has reached the target location (e.g., to ensure the catheter tube 100 is not drifting away from the target location). By performing insufflation via the channel 111, visualization (e.g., as represented in the captured image data generated by the imaging device 108) of internal structures (e.g., gastro-intestinal structures) of the subject into which the catheter tube 100 is inserted may be improved. This improved visualization may also improve the recognition of landmarks that may be achieved by the AI model(s). Topographic and/or visual (e.g., two dimensional) image data acquired by the imaging device 108 as the catheter tube 100 and the articulated stylus maneuver through the enteral system may be saved in a computer memory of the remote device for simultaneous interpretation by AI models/algorithms or for later interpretation of the captured image data by qualified personnel for identification of abnormal tissue in the enteral cavity.

Figure 2:
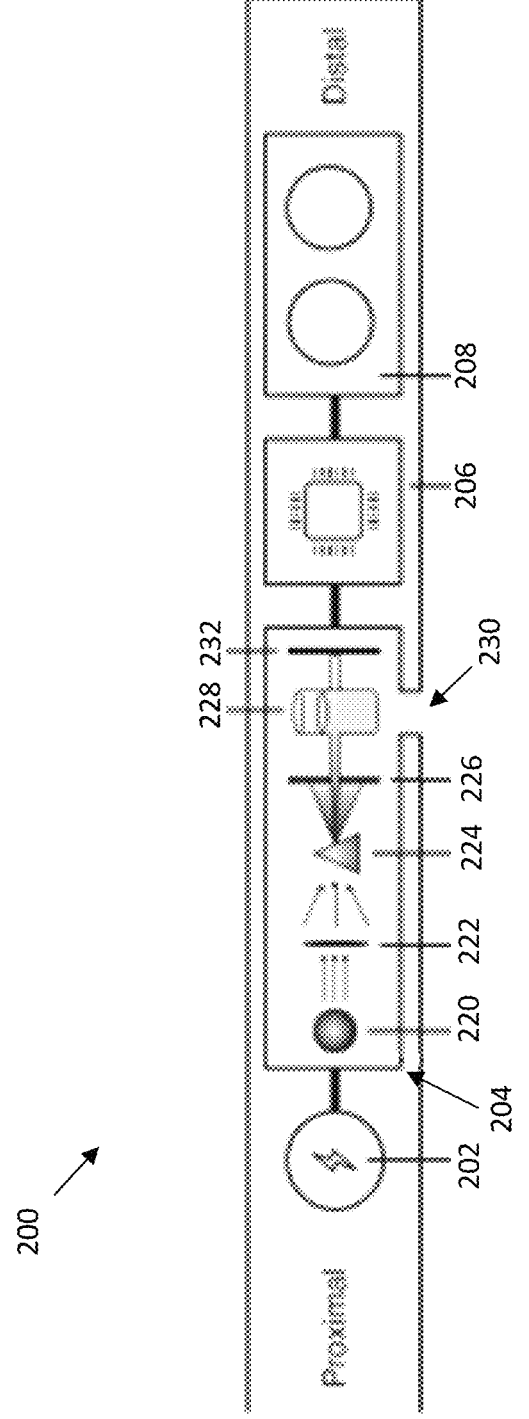
FIG. 2 illustrates an exemplary block diagram of circuitry within a distal end of a catheter tube, the circuitry including a battery, a spectrometer, a transceiver, and an imaging device, and a channel that may or may not be used for insufflation of the gastro-intestinal tract during placement of the device.

FIG. 2 shows an illustrative block diagram of devices and components within a distal end of a catheter tube 200 (e.g., which may correspond to the catheter tube 100 of FIG. 1A). The catheter tube 200 may include a battery 202 (e.g., corresponding to the battery 102 of FIG. 1A), a spectrometer 204 (e.g., corresponding to the spectrometer 204 of FIG. 1A), a transceiver 206 (e.g., corresponding to the transceiver 106 of FIG. 1A), and an imaging device 208 (e.g., corresponding to the imaging device 108 of FIG. 1A). In some embodiments, the spectrometer 204 may be a spectrophotometer. The spectrometer 204 may include a light source 220, a collimator 222, a monochromator 224, an exit slit 226, a sampling module 228, an access point 230, and a detector 232. The light source 220 may include one or more light emitting diodes (LEDs). The collimator 222 may include a lens that focuses the light generated by the light source 220 onto the monochromator 224 (e.g., through an entrance slit thereof, not shown). The monochromator 224 may include a prism (e.g., such as a Bunsen prism monochromator) or other optical device that transmits, to the sampling module 228 through the exit slit 226, a mechanically selectable narrow band of wavelengths of wavelengths of light received from the collimator 222. The size of the exit slit 226 may be affect the wavelength(s) of light that may be output through the exit slit 226. Light (e.g., light output through the exit slit 226) passing through sampled material in the sampling module 228 be received by the detector 232. For example, the detector 232 may be a photodetector that measures the magnitude of the light that is able to pass through the sample, from which the absorbance and/or percent transmittance of the sample for the wavelength of the light may be determined.

Based on the absorbance and/or percent transmittance of the sample determined from the magnitude of light detected by the detector 232, the chemical make-up of the sample may be identified. For example, identification of the sample may be based on known spectroscopy properties of a compound (e.g., the sample) being studied. For example, the spectral wavelength of the compound may be determined, and using algorithms or models located in the RCDC, or in the cloud may be applied to identify the compound based on the spectral wavelength. For example, biomarkers that may be sampled and identified using the spectrometer 204 may include, but are not limited to, sodium, potassium, osmolarity, pH, medications, illicit drugs, digestive enzymes, lipids, fatty acids, blood, blood products, biomarkers for gastric cancer and/or gastric inflammation, biomarkers for intestinal cancer and/or intestinal inflammation, gastric proteome, and/or intestinal proteome.

Figure 4A:
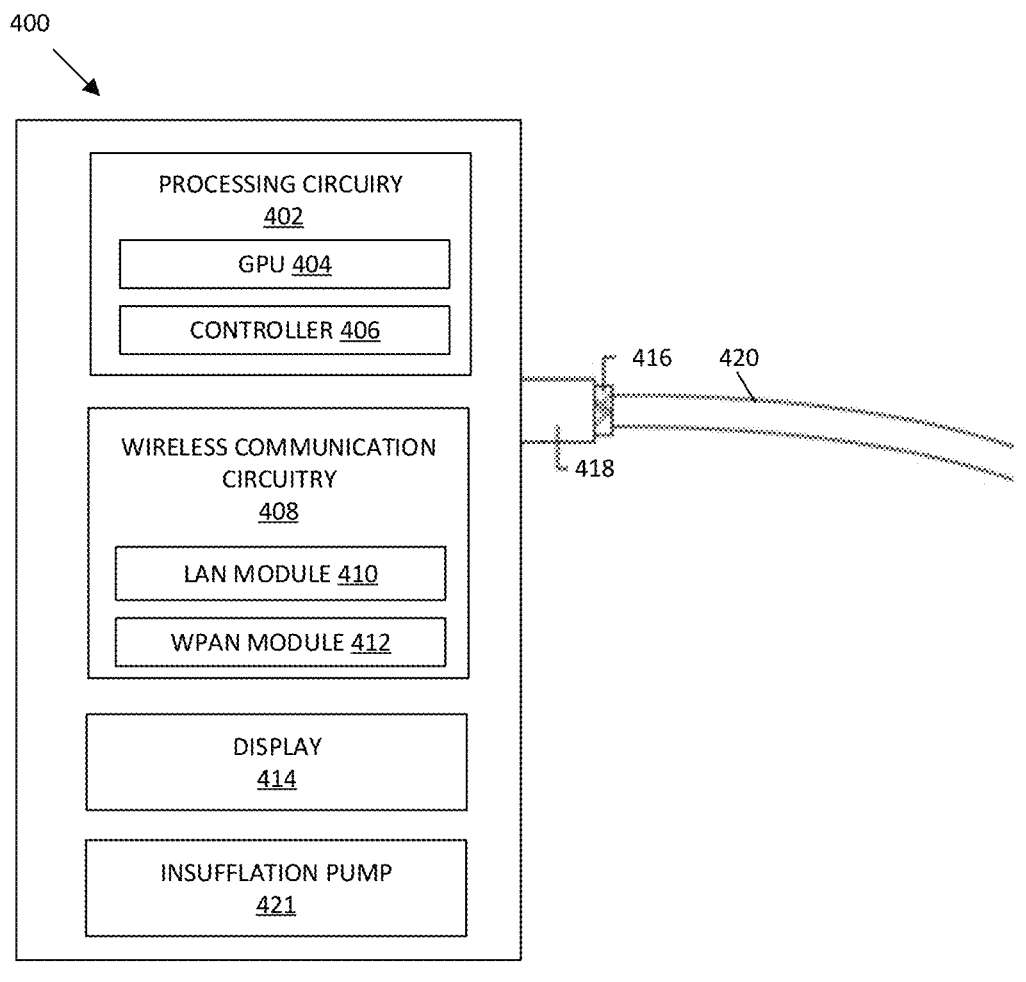
FIGS. 4A and 4B illustrate an exemplary robotic control and display center (RCDC) that may guide a catheter enteric tube to a target location within the enteral system or respiratory tract of a subject via an articulated stylet having an articulated end that is controlled according to navigation data generated by an artificial intelligence model to direct the tube to the target location in an enteral cavity or respiratory tract.
Figure 4B:
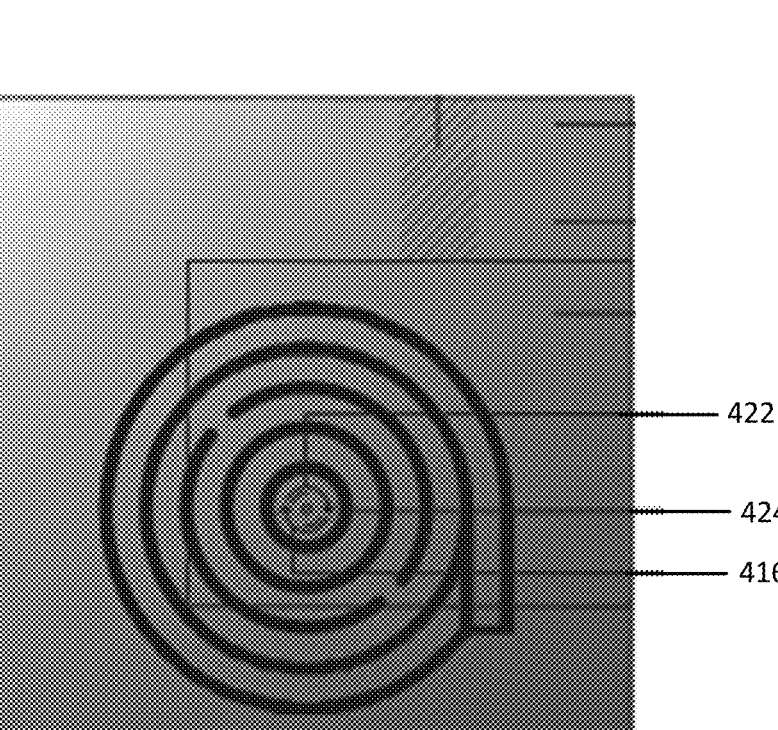

In some embodiments, analysis to determine the identity of a substance sampled by the spectrometer 204 may be performed by a processor of a remote computing device (e.g., the GPU 404 of the device 400 of FIGS. 4A and 4B). In some embodiments, this analysis may be performed using one or more processors of a cloud computing environment.

Figure 3:
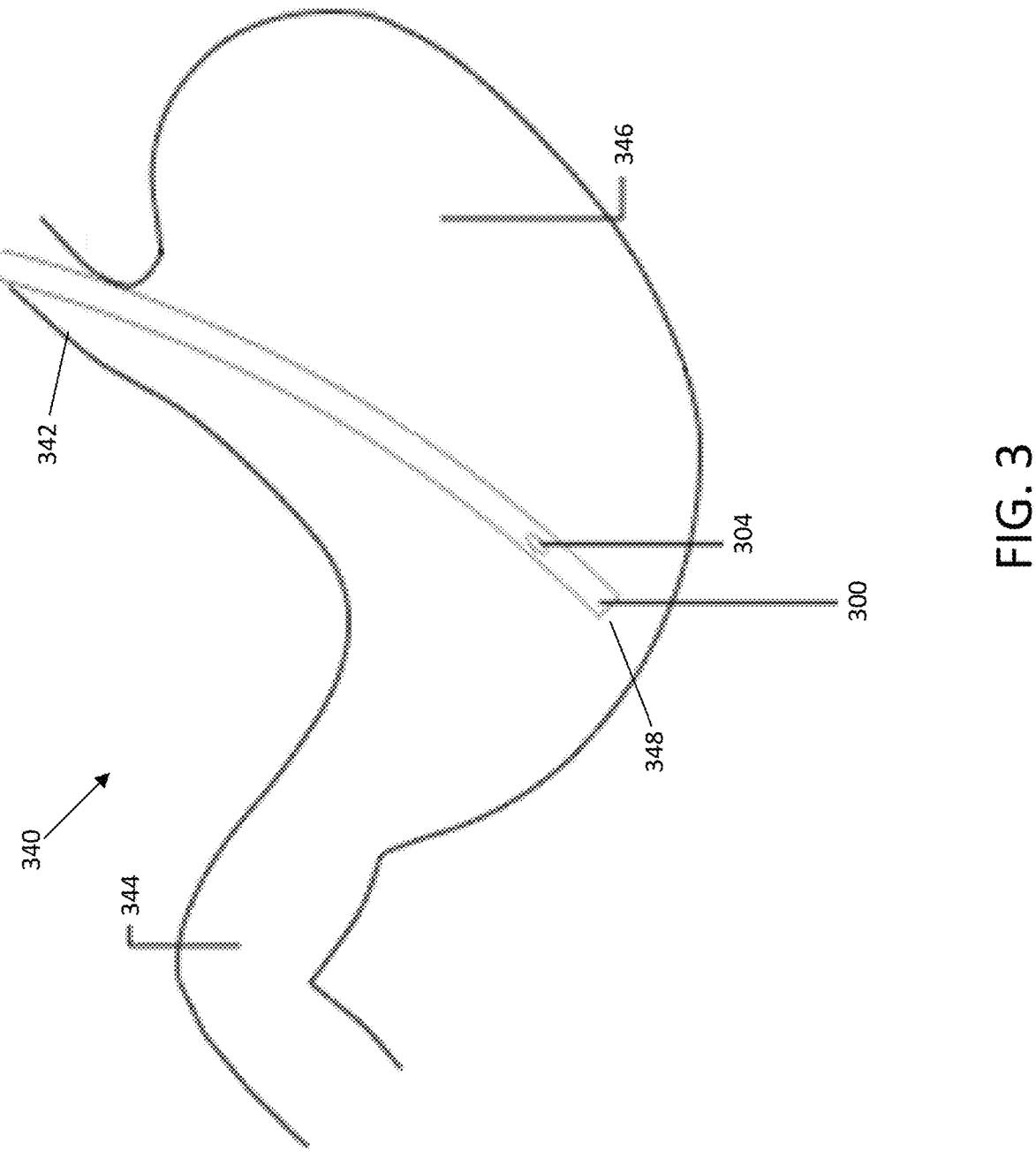
FIG. 3 illustrates a placement of an exemplary catheter tube within the stomach of a subject.
Figure 11:
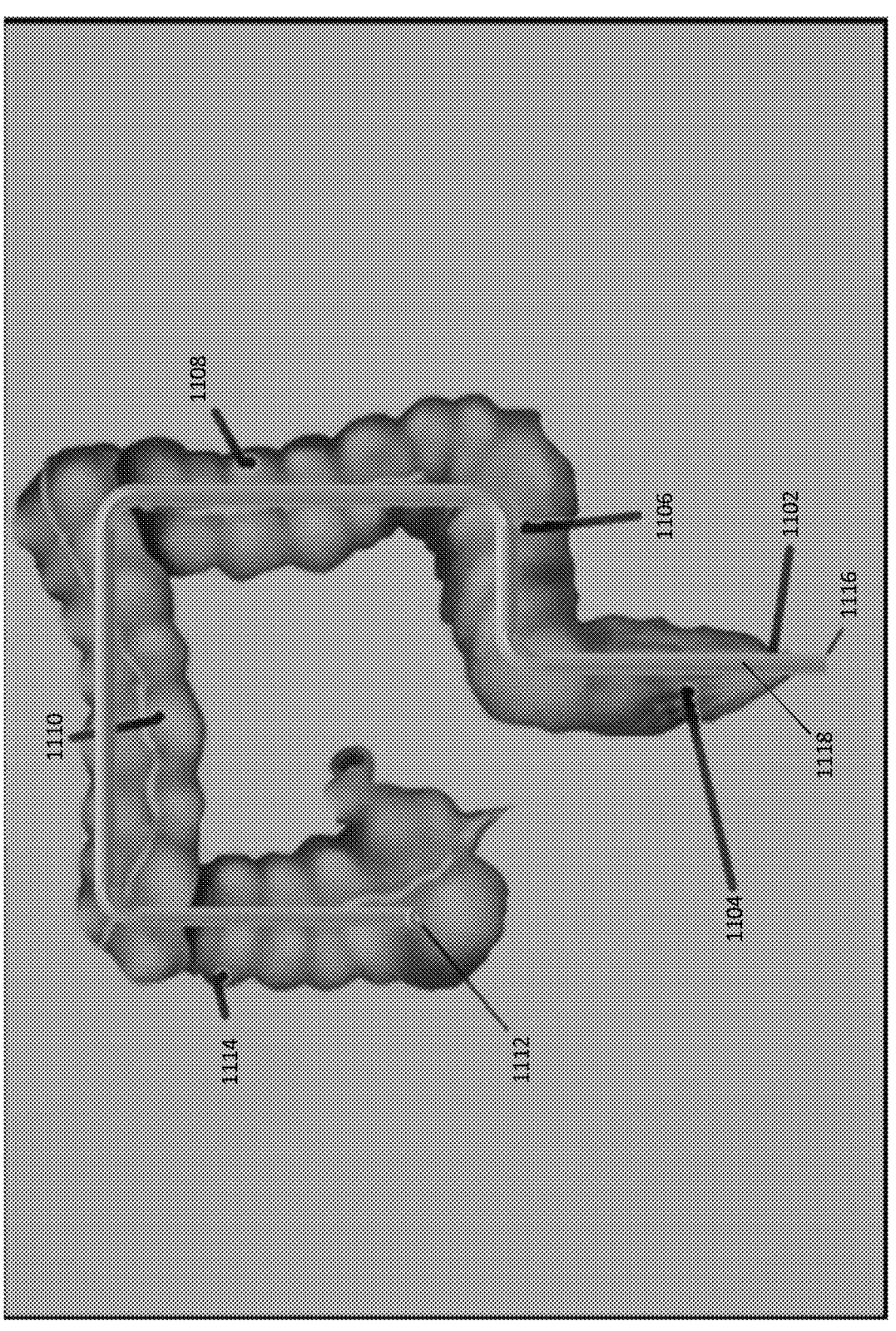
FIG. 11 illustrates a view of an exemplary articulated stylet that has been driven to a target location through the enteral space of a portion of a subject's intestines.
Figure 12A:
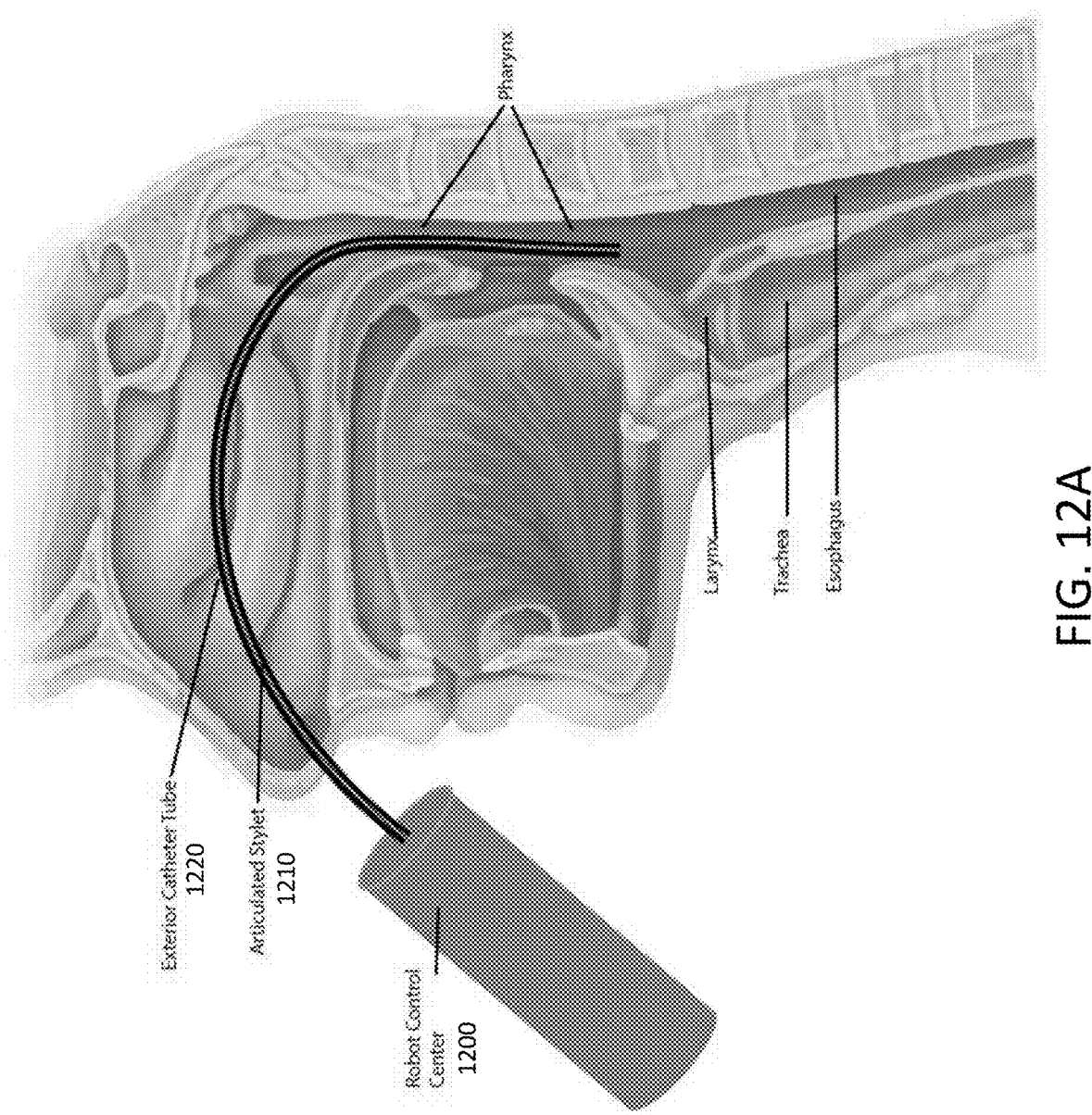
FIGS. 12A, 12B, and 12C illustrate the robot advancing the catheter device with its inner articulated stylet and the exterior catheter tube, demonstrating the self-driving robot advancing to the inflection point of the larynx where the robot can turn either anteriorly into the larynx and trachea or posteriorly into the esophagus.
Figure 12B:
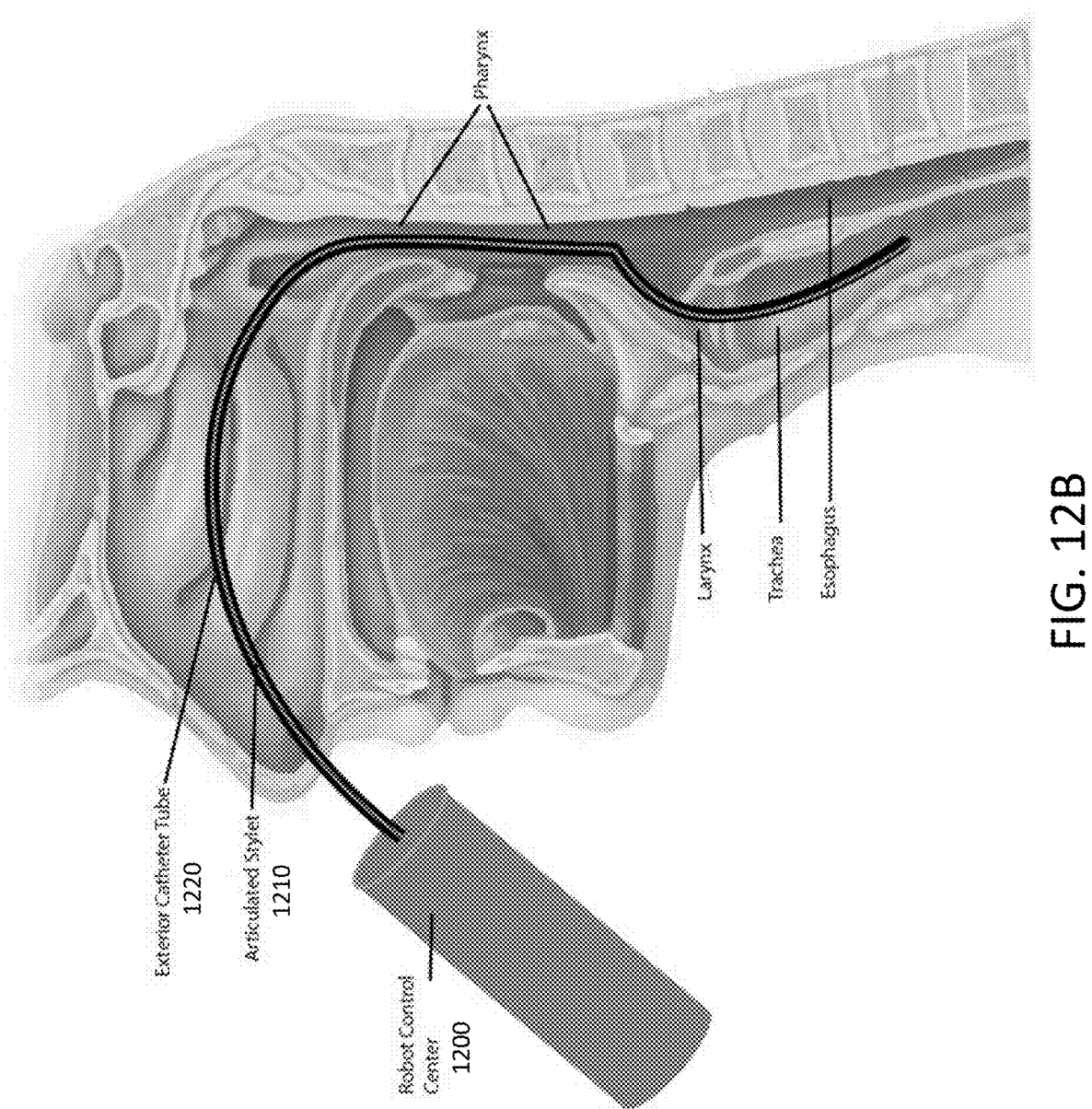
Figure 12C:
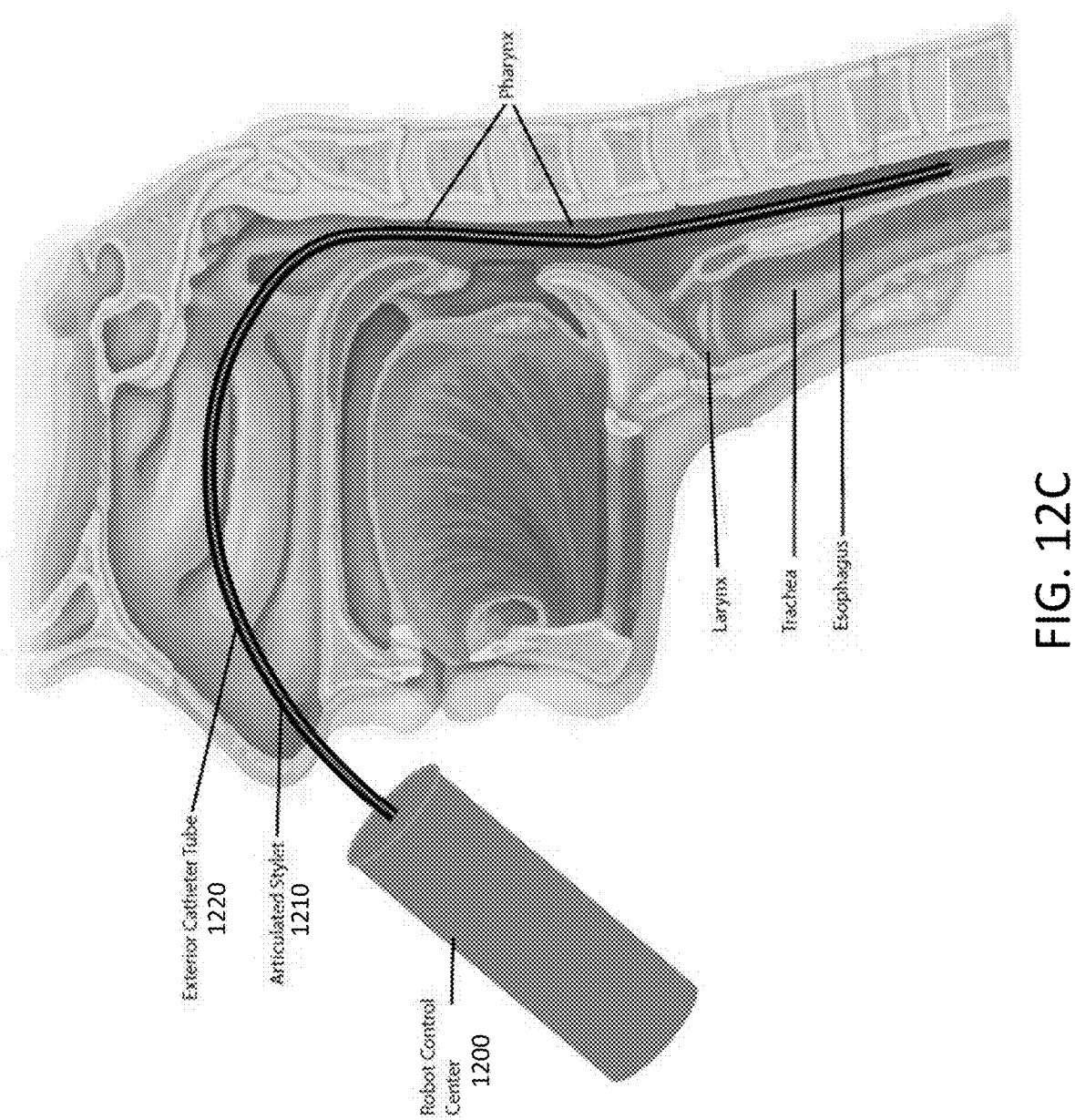

FIGS. 3 and 12C show examples of the placement of a catheter tube 300 (e.g., corresponding to catheter tube 100 of FIG. 1A or catheter tube 200 of FIG. 2) within an enteral system 346 of a subject (e.g., within the subject's gastrointestinal tract). As shown, the enteral system 346 may include a stomach 346, duodenum 344, and an esophagus 342. The catheter tube 300 may be driven (e.g., automatically, without manual guidance from a clinician) through the esophagus 342 to a target location at the pyloric antrum 348 of the stomach 346. In some embodiments, the catheter tube 300 may be driven to other target locations within the enteral system 346, such as the duodenum 344, other parts of the stomach 346, or other parts of the small or large intestine of the subject. Likewise, the area of access to the enteral system may be through the rectal region for placement and analysis for the lower enteral tract, as shown in FIG. 11, or in the pulmonary tract as demonstrated in FIG. 12B.

Once the tip of the catheter tube 300 has reached the target location one or more procedures may be performed using the catheter tube 300. For example, external content (e.g., medication, enteral feedings, or other biologically or chemically active substances, respiratory support, ventilation) may be delivered to the target location through the catheter tube, intestinal (including large bowel) content or stomach content may be removed (e.g., biopsied), and/or biomarkers (e.g., physical and/or biochemical biomarkers) may be continuously sampled using a spectrometer (e.g., spectrometer 104, 204 of FIGS. 1A, 1C, 2) disposed in the distal end of the catheter tube 300. In addition, all enteric/tracheal imaging data obtained during the placement of the catheter tube 300 in the enteral tract may be stored and analyzed (e.g., simultaneously analyzed) by one or more AI models/algorithms or subsequently by qualified personnel for identification of abnormal tissue in the enteral/tracheal cavity.

FIGS. 4A and 4B show a device 400 (sometimes referred to herein as a robotic control and display center (RCDC) 400) for the robotic control of an articulated stylet that may be inserted into the lumen (e.g., lumen 110 of FIGS. 1B-1E) of a catheter tube (e.g., catheter tubes 100, 200 of FIGS. 1A, 2) to automatically drive the distal end of the catheter tube to a target location within the body of a subject. The device 400 may include processing circuitry 402, wireless communication circuitry 408, a display 414, a 420, an insufflation pump 421, a screw-based lock mechanism 416, a wire motor control 418, a robotic control engine 424, a thread drive 422, and a loading dock 426.

The processing circuitry 402 may include a graphics processing unit (GPU) 404 and a controller 406 (e.g., which may include one or more computer processors). The processing circuitry may execute computer-readable instructions stored on one or more memory devices (not shown)

included in (e.g., as local storage devices) or coupled to (e.g., as cloud storage devices) the device 400. For example, executing the computer-readable instructions may cause the processor to implement one or more AI models. These AI models may include, for example, one or more trained machine learning models, such as decision tree models, naïve Bayes classification models, ordinary least squares regression models, logistic regression models, support vector machine models, ensemble method models, clustering models (e.g., including neural networks), principal component analysis models, singular value decomposition models, and independent component analysis models.

For example, a neural network may be implemented by the processing circuitry 402 that receives a target location within the enteric cavity of a subject along with a stream of images (e.g., enteral/tracheal images captured/generated by the imaging device 108 of FIG. 1 and sent to the device 400 via the wireless communication circuitry 408) of features (e.g., organ tissue) around a catheter tube (e.g., catheter tube 100, 200 of FIGS. 1A, 2), and that outputs instructions that control the robotic control engine 424 and the articulated stylet 420 based on the received images, causing the articulated stylet 420 to move through the enteric cavity or respiratory tract of the subject until the catheter tube reaches the target location. The neural network may, for example, be trained and verified using 3D models of human enteric/respiratory pathways and anatomic images of naso/oral/rectal enteric and tracheal trajectories corresponding to catheter tube placement in multiple (e.g., thousands) of human subjects.

In some embodiments, the processing circuitry 402 may execute a volume sensing module configured to obtain volume measurements of an enteral space into which the catheter tube has been inserted. The volume measurements may be calculated based on three-dimensional volumetric data generated/acquired using one or more imaging techniques such as hyperspectral imaging, time of flight imaging using multiple wavelengths of light, and stereo imaging. The volume sensing module may, based on the volume measurements, determine a first volume value corresponding to a total volume of the enteral space, a second volume value corresponding to a first portion of the total volume that is empty, and a third volume value corresponding to a second portion of the total volume that is filled with material. The third volume may be calculated by subtracting the second volume from the first volume.

For example, the artificial intelligence (AI) based detection and tracking model which enables the RCDC to traverse autonomously may use a deep-learning detector, which may include both a deep-learning YOLO-based detector and convolutional neural network (CNN), to detect the nasal, oral, and rectal orifices, and the enteral/respiratory cavities, by further distinguishing between visually similar structures in the proximal environment. For enteral/tracheal spatial detection, a 26-layer or greater CNN based detection model may be employed. In such a model, the first 24 layers may be fully convolutional layer that are pre-trained on Imagenet dataset, and the final two layers may be fully connected layers which output the detected tissue/organ. For tracking, a median-flow filtering based visual tracking technique to predict the motion vector for the robotic placement device may be employed, using estimations of the location of an object with sparse optical flow. The tracking based system may be based on the assumption that an object consists of small and rigidly connected blocks or parts which more synchronously together with motion of the whole object, such as the enteral cavity or respiratory tract.

For example, the AI model initialization may be achieved by establishing a bounding box in which the nasal/oral/rectal orifice or enteral cavity is located at first, and within this region of interest a sparse grid of points may be generated. The motion of the enteral structure detected by optical flow in the captured images may be computed as the median value of differences between coordinates of respective points that are in the current and preceding images. Only those points which have been regarded as reliable during the filtering may be considered, such that the algorithm may estimate the object scale variations.

For example, the AI model implementation and enteral/tracheal object detection may be accomplished via YOLO-based algorithm and object tracking that may be accomplished via median flow tracker, as implemented through Python. The environment may be built on Ubuntu. The graphics processing unit (GPU) integration cuDNN and CUDA toolkit may be used. The training segment may be implemented by supplying annotated images to Keras implementation of YOLO. The Keras and TensorFlow backend may be used, and the dataset may be created with annotated software VoTT (Microsoft, Redmond, WA), with an adopted learning rate of $10^3$ for 1,000 training epochs and saved model parameters every 100 epochs. The detection segment may again be implemented based on Keras running TensorFlow on the backend. For tracking, the tracking API in OpenCV may be used. The bounding box may be detected by YOLO and passed to Median Flow tracker at m:n ratio, in order to realize real-time detection and tracking.

In some embodiments, rather than being stored and executed by the processing circuitry 402, the computer-readable instructions corresponding to the AI models may be stored and executed by cloud-based memory devices and computer processors. Data (e.g., image and spectrometer data) taken as inputs by the AI models may be sent to such cloud-based memory devices and computer processors by the device 400 via one or more communication networks using the wireless communication circuitry 408. The wireless communication circuitry 408 may additionally receive the outputs of these AI models after they have processed the data. In this way, the requirements for the processing capabilities of the local processing circuitry 402 of the device 400 may be less than if the AI models needed to be executed locally, which may generally decrease the cost and, in some cases, the footprint of the device 400. However, such cloud-based solutions generally require network (e.g., internet) connectivity and may take longer to execute the AI models than local hardware (e.g., in cases where cloud and local processing capabilities are assumed to be equal). In some embodiment, AI models may be executed to perform data analysis by both the local processing circuitry 402 and cloud-based processors (e.g., such that biomarker analysis is performed locally and robotic driven navigation analysis is performed by cloud-based processors, or vice-versa).

The wireless communication circuitry 408 may include a local area network (LAN) module 410 and a wireless personal area network (WPAN) module 412. The LAN module 410 may communicatively couple the system 400 to a LAN via a wireless connection to a wireless router, switch, or hub. For example, the LAN module 410 may communicate with one or more cloud computing resources (e.g., cloud computing servers) via network connections between the LAN and an external network to which the cloud computing resources are connected (e.g., over a wide area network (WAN) such as the internet). The WPAN module 412 may communicate with a transceiver (e.g., transceiver 106, 206 of FIGS. 1A, 1D, 2) disposed at a distal end of the catheter tube using one or more antennas according to a short-wavelength UHF wireless technology standard (e.g., Bluetooth®) via an established WPAN. For example, the WPAN module 412 may receive image data (e.g., 3D topographic image data) generated by an imaging device (e.g., imaging device 108, 208 of FIGS. 1A, 1E, 2) disposed in the distal end of the catheter tube, which may be a topographic imaging device. The image data may be transmitted to the WPAN module 412 in real-time as the catheter tube is driven toward the target location in the subject's enteric cavity or respiratory tract. The WPAN module 412 may also receive spectrometer data from a spectrometer (e.g., spectrometer 104, 204 of FIGS. 1A, 1C, 2). The WPAN module 412 may provide this spectrometer data to the processing circuitry 402, which may analyze the spectrometer data to identify one or more chemical substances sampled by the spectrometer (e.g., using one or more of the AI models trained to perform such analysis).

In some embodiments, rather than using the WPAN module 412 to communicate with the communication circuitry (e.g., transceiver) disposed in the distal end of the catheter tube, a direct wired connection to the communication circuitry or the LAN module 410 may be used to transfer data to and from the communication circuitry of the catheter tube.

The articulated stylet 420 (sometimes referred to herein as a "robotic navigating articulated stylet") may be inserted into the lumen (e.g., lumen 110 of FIGS. 1B-1E) of a catheter tube (e.g., catheter tube 100, 200 of FIGS. 1A, 2). The articulated stylet 420 may be locked to a port of the device 400 using a screw-based lock mechanism 416. The screw-based lock mechanism 416 could work in several different ways. In one embodiment, the screw-based lock mechanism 416 may operate similarly to a Tuohy Borst valve or a standard coaxial articulated stylet lock that screws down a silicone or elastomer ring that would compress around the articulated stylet 420 to lock it in place. In another embodiment, the screw-based lock mechanism 416 could include a screw/wedge aligned substantially perpendicularly to the length of the articulated stylet 420, which may to "pinch" the articulated stylet 420 as the screw/wedge is rotated into a "locked" state, locking the articulated stylet 420 in place. In yet another embodiment, the screw-based lock mechanism 416 may include a colt mechanism that includes a coaxial screw mechanism that operates by bringing several metal (or plastic) fingers in around the articulated stylet 420 as the mechanism is rotated to lock the articulated stylet 420 in place (e.g., similar to a drill bit chuck). In some embodiments, the articulated stylet 420 may be embedded in the catheter tube itself, rather than being inserted into the lumen of the catheter tube. The articulated stylet 420 may be formed from one of a variety of applicable materials. In some embodiments, the articulated stylet 420 may be formed from stainless steel. For example, the articulated stylet 420 may include a single stainless steel filament or a braided or wound stainless steel cable. In some embodiments, the articulated stylet 420 may be made from Nitinol, which may provide shape memory or extreme flexibility characteristics. The articulated stylet 420 may have an articulated distal end (e.g., articulation 504 of FIG. 5A, 5B), which may be controlled by the robotic control engine 424, such that the articulated stylet 420 may change direction as it guides the catheter tube through the enteral cavity or respiratory tract of a subject. For example, the robotic control engine 424 may directly navigate the articulated stylet 420, and therefore the catheter tube, from an access site (e.g., the nose or mouth of the subject) through the subject's enteral cavity or respiratory tract until the distal end of the articulated stylet 424 and the catheter tube reaches its destination. The robotic control engine may control the direction of the articulated stylet 420 based on navigation data output by a navigation AI model of the AI models that may be executed by the processing circuitry 402 and/or cloud-based processing circuitry in communication with the wireless communication circuitry 408. In some embodiments, more than just the distal end of the articulated stylet 420 may be articulated, with additional articulations being included along some or all of the length of the articulated stylet 420. In this way, the articulated stylet 420, as controlled by the robotic control engine 424 may steer the catheter tube to a target location in the subject's enteral cavity or respiratory tract, while avoiding areas that may pose safety risks to the subject, such as the subject's larynx, vocal cords, and lower airway. The robotic control engine 424 may additionally apply a robotic feedback system once the catheter tube has reached its target location in the subject's enteric cavity or respiratory tract, the robotic feedback system maintaining the catheter tube at the target location (e.g., by continuously monitoring the position of the distal end of the catheter tube using one or more AI models based on topographic image data generated by an imaging device embedded in the catheter tube). Various mechanisms of control may be carried out by the robotic control engine 424 to control the movement of the articulated distal end of the articulated stylet. In some embodiments, the mechanism of control may include a pull-wire type configuration where multiple wires are attached at different points in the catheter tube around locations (e.g., articulation joints) where movement (e.g., bending/flexing) of the catheter tube is desired. These wires would be connected to spools in the motor mechanism of the robotic control engine 424. The spools may rotate in a first direction (e.g., clockwise or counterclockwise) to wind the wires up (flexing the catheter tube tip back toward its proximal end) and may rotate in a second direction (e.g., opposite the first direction) extend the wires (e.g., causing the catheter tube to stop flexing). Positioning these wires at "strategic" points along the longitudinal axis (e.g., length) of the catheter tube could allow steering of the catheter tube in nearly any direction. In another embodiment, of this mechanism of control could utilize a series of links disposed inside the catheter that could be addressed via multiple Nitinol wires that are coupled to the series of links. When a current is supplied to the Nitinol wires (e.g., supplied by a power supply controlled by the robotic control engine 424), the Nitinol wires shrink, flexing the catheter. Remove the current causes Nitinol wires to relax, extending the catheter.

For advancement and retraction of the articulated stylet 420, a drive system (e.g., a drive rod, worm gear, or rack and pinion based drive system, depending on the accuracy required) may be included in the robotic control engine 424 that may be controlled to drive the articulated stylet forward and back (e.g., using a single motor). A transmission may be included in the robotic control engine 424, which may be used to enable automatic rotation and articulation of the catheter when the articulated stylet 420 is inserted, as well as the forward/reverse driving of the articulated stylet 420. The transmission would also enable steering.

A display 414, which may be an electronic display including an LCD, LED, or other applicable screen, may be included in the device 400. The display 414 may display the status information related to the articulated stylet, the catheter tube, the components of the catheter tube, and one or more organs of a subject that are proximal to the distal end of the catheter tube. For example, the displayed data may include information regarding placement of the catheter tube (e.g., the tip and/or distal end of the catheter tube), the status of the components of the catheter tube, and biomarkers detected by the spectrometer embedded in the distal end of the catheter tube. In some embodiments, some or all of the information shown on the display 414 may also be transmitted to other electronic devices by the LAN module 410 and subsequently displayed on such devices. For example, such electronic devices may include personal electronic devices phones and tablets of doctors and nurses, as well as computer systems having a monitors disposed at subjects' bedsides, any of which may be connected to the same LAN as the LAN module 410. Data transmitted to these devices may be stored as part of an Electronic Health Record for the corresponding subject, and may be incorporated in to Clinical Decision Support Systems (e.g., for use in patient management).

An insufflation pump 421 may be included in the RCDC 400, which may be an air pump, carbon dioxide pump, or any applicable pump configured to output a gas (e.g., a gas appropriate for use in insufflation). The insufflation pump 421 may be coupled to an insufflation channel (e.g., channel 111, 511 of FIGS. 1A-1E, 5C), through which insufflation of an interior cavity of a subject (e.g., a gastro-intestinal tract of the subject) may be performed.

The thread drive 422 may control the extension and retraction of the articulated stylet 420, according to navigation data output by the navigation AI models described previously.

The loading dock 426 may store the portion of the guide-wire that is not in use. The articulated stylet 420 may be longer than the catheter to be placed, such that the catheter tube can be driven forward fully without utilizing the full length of the articulated stylet 420. In some embodiments, the articulated stylet 420 may run on a spool or through a linear tube of the loading dock 426, depending on the application and/or the drive mechanism. In some embodiments, the articulated stylet 420 may be loaded and addressed by the thread drive 422 by feeding the articulated stylet tip into the drive gears/rod/rack of the thread drive 422. In some embodiments, the length of the articulated stylet 420 may be selected to accommodate having the thread drive 422 far enough from the patient to allow for the RCDC to be positioned at the side of the patient's bed. In such embodiments, fixation may be provided for the articulated stylet 420 at the patients mouth (e.g., via a biteblock) in order to improve the mechanical drive of the articulated stylet 420.

Figure 5A:
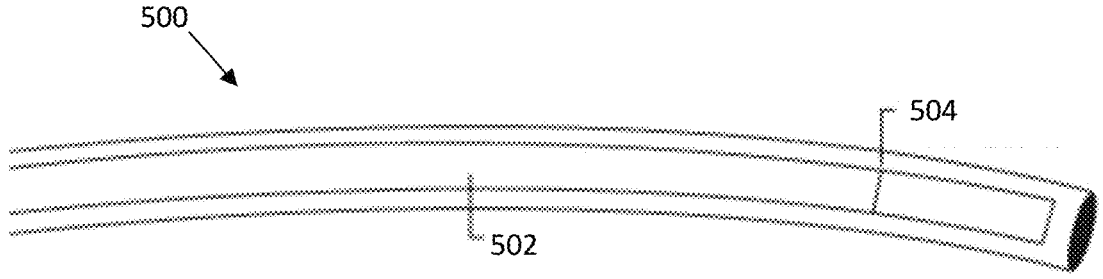
FIGS. 5A through 5C illustrate an exemplary catheter enteric tube into which an articulated stylet has been inserted.

FIG. 5A shows an illustrative placement of a, articulated stylet 502 (e.g., articulated stylet 420 of FIGS. 4A, 4B) in a catheter tube 500 (e.g., catheter tube 100, 200 of FIGS. 1A-1E, and 2) to form a catheter assembly. The articulated stylet 502 may include a distal end having an articulation 504, which may have three degrees of freedom by which it may navigate through three-dimensional space, which may include use of plunge, rotation, and deflection of the articulation 504. For example, the articulation 504 may be located around 10 cm away from the distal end of the articulated stylet 502. An illustrative placement of an insufflation channel 511 (e.g., channel 111 of FIG. 1) in a tube wall of the catheter tube 500 is shown.

Figure 5B:
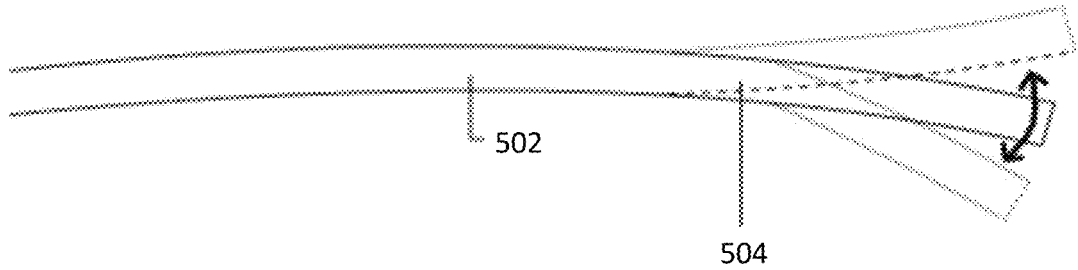

FIG. 5B shows an illustrative range of motion of the distal end of the articulated stylet 502 as the articulation 504 is controlled by a robotic control engine (e.g., robotic control engine 424 of FIG. 4A) of an RCDC device (e.g., device 400 of FIG. 4A, 4B), such that the robotic control engine may navigate the articulated stylet 502, and thereby the catheter tube 500, to a target location within the enteral system or respiratory tract of a subject.

Figure 5C:
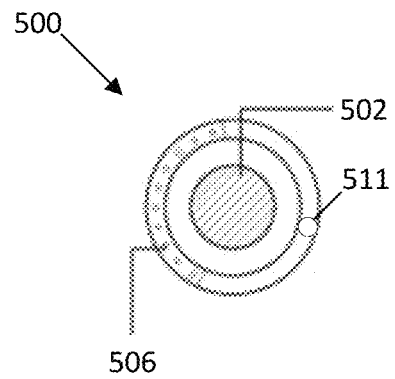

FIG. 5C shows a cross-section of a distal portion of the catheter tube 500 when the articulated stylet 502 is fully inserted into the catheter tube 500. As shown, when fully inserted, the articulated stylet 502 may overlap with one or more embedded components of the catheter tube, such as an imaging device (e.g., imaging device 108 of FIG. 1) embedded in a tube wall 506 of the catheter tube 500.

FIG. 6 shows an illustrative process flow for a method 600 by which one or more AI models may be implemented to navigate an articulated stylet (e.g., articulated stylet 420, 502 of FIGS. 4A, 5A-5C) and catheter tube (e.g., catheter tube 100, 200, 500 of FIGS. 1A, 2, 5A) to a target location within a subject's enteral system. For example, the method 600 may be performed by executing computer-readable instructions stored on one or more local storage devices of a computer system (e.g., device 400) or remote storage devices (e.g., cloud-based storage devices coupled to the computer system via an electronic communication network), using one or more computer processors (e.g., processing circuitry 402 of FIG. 4, or cloud-based processing circuitry coupled to the computer system via an electronic communication network).

At step 602, the catheter tube, with the articulated stylet fully inserted, is introduced from an external body location of a subject. For example, the external body location through which the catheter tube is introduced may be the subject's mouth, nose, rectum, or a surgical incision on the subject's body.

At step 604, the catheter tube may be navigated, by driving the articulated stylet, toward a target location within the subject's body (e.g., within an enteral cavity of the subject). The navigation of the catheter tube may be performed by extending the articulated stylet into the body of the subject and controlling the direction, rotation, and movement of at least an articulated distal end of the articulated stylet using a robotic control engine (e.g., robotic control engine 424 of FIGS. 4A, 4B).

At step 606, an imaging device (e.g., imaging device 108 of FIGS. 1A, 1E) included in the catheter tube may capture (e.g., continuously capture) image data, such as 3D topographic image data, time of flight image data, visual (e.g., 2D) image data, and/or other applicable enteric/tracheal image data, of structures (e.g., organ tissue) in proximity to the distal end of the catheter tube. The imaging device may send the captured image data to a transceiver included in the distal end of the catheter tube. The captured image data may be stored at a computer memory that is included in or communicatively coupled to the robotic control engine. Once store, the captured image data may be analyzed simultaneously (e.g., in near-real time) by one or more AI algorithms/models or may be subsequently analyzed by qualified personnel to identify abnormal tissue in the enteral cavity.

At step 608, the transceiver may wirelessly transmit the captured image data to processing circuitry (e.g., processing circuitry 402 of FIG. 4A) of a computer system. This wireless transmission may be performed via communication between the transceiver and a WPAN module (e.g., WPAN module 412) of the computer system.

At step 610, the processing circuitry of the computer system may execute one or more AI models (e.g., navigation AI models that may include a neural network). The AI models may receive the captured image data as inputs and, after processing the captured image data through a neural network and/or median-flow filtering, may output navigation data to the robotic control engine. The navigation data may include instructions for how the robotic control engine should manipulate, articulate, rotate, and/or drive the articulated stylet toward the target location, and may further include information defining a position of the catheter tube in the enteral cavity or respiratory tract of the subject.

At step 612, the processing circuitry may determine the current location of the catheter tube tip based on the navigation data. The processing circuitry may further determine whether the current location of the catheter tube tip corresponds to the target location.

At step 614, if the current location of the catheter tube tip is determined to correspond to the target location, the method 600 proceeds to step 616. Otherwise, the method 600 returns to step 604, and the robotic control engine continues to navigate the catheter tube and articulated stylet based on the navigation output by the AI models.

At step 616, the articulated stylet is removed from the catheter tube, and an operation is performed using the catheter tube. For example, substances (e.g., nutritive substances, medicine, or ventilation) may be delivered to the target location of the subject's enteral cavity or respiratory tract through a lumen of the catheter tube. Alternatively, substances (e.g., biopsied tissue or fluids) at the target location of the subject's enteral cavity may be retrieved through the lumen of the catheter tube.

In some embodiments, the catheter tube may remain indwelling in the patient for a standard duration of time following step 616, as clinically indicated. The indwelling catheter tube may be used for continuously monitoring, continuously sampling, providing food, delivering medicine, or providing airway support.

Figure 7:
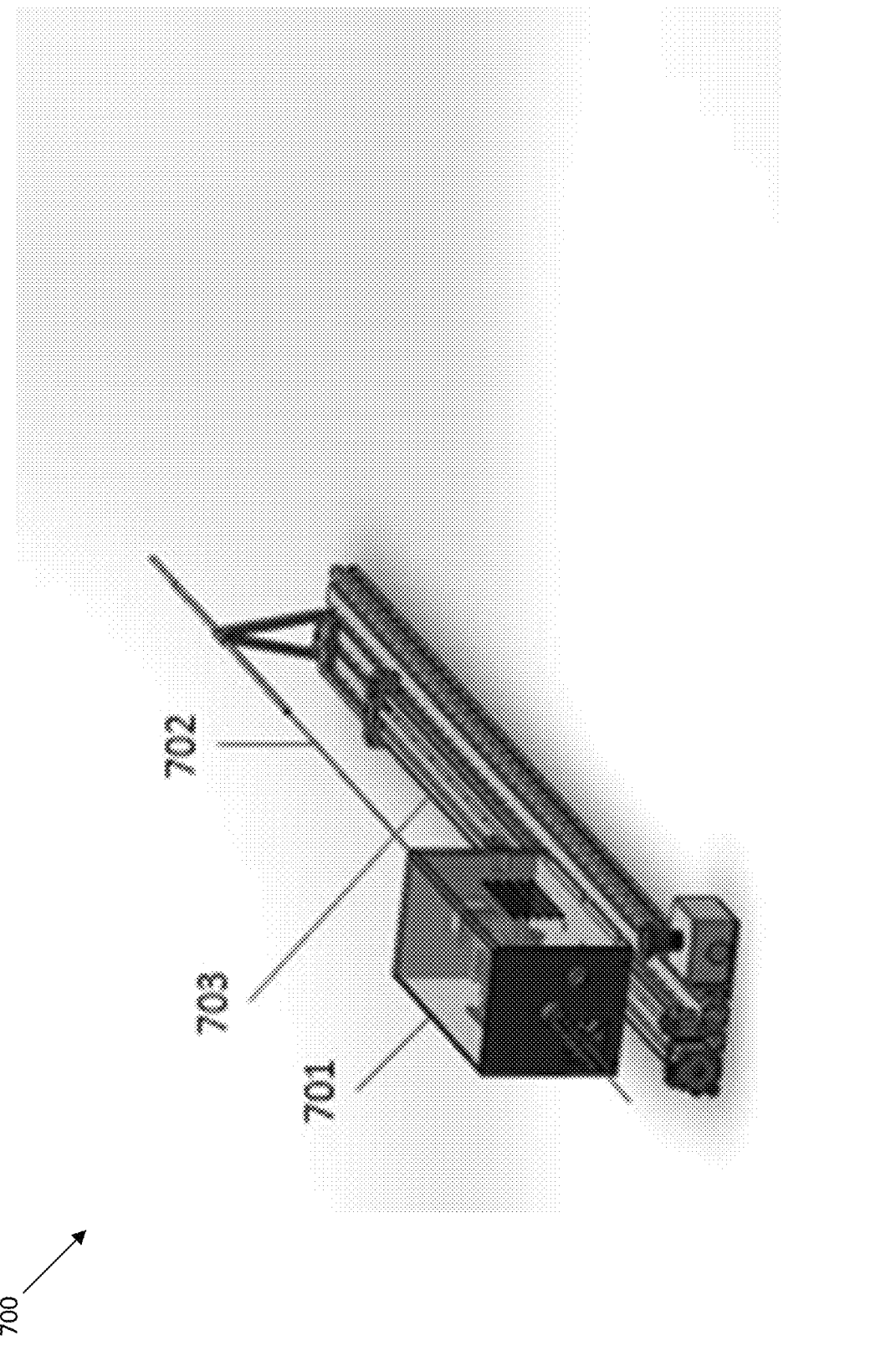
FIG. 7 illustrates an isometric view of an exemplary robotic control system that may manipulate a catheter tube into a desired location.

FIG. 7 shows a potential embodiment of an RCDC (e.g., which may correspond in whole or in part to the RCDC 400 of FIGS. 4A and 4B). The example RCDC 700 may include a carriage 701, an articulated stylet 702, and a slide 703. The carriage 701 may house imaging devices and motors that may move with the catheter into which the articulated stylet 702 is inserted. The articulate stylet 702 may be mounted to the carriage 701. The carriage 701 moves along the slide 703 to control the position of the tip of the articulated stylet 702. A controllable motor (e.g., linear slide motor 802, FIG. 8A) may drive the movement of the carriage 701 along the slide 703, For example, the controllable motor may move the carriage 701 along the slide 703 according to instructions received by the controllable motor from a computer processor (e.g., processing circuitry 402, FIG. 4A) of the RCDC 700.

Figure 8A:
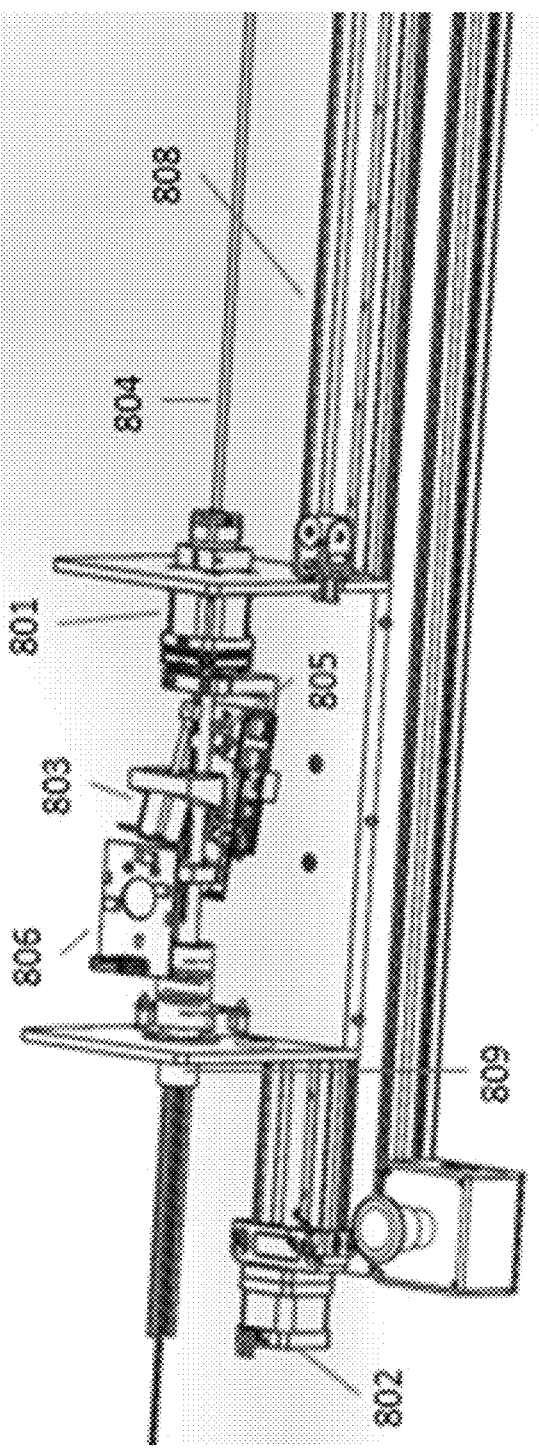
FIGS. 8A through 8B illustrates respective isometric and top views of a carriage that may be included in a robotic control system, which may contain an imaging device coupled to an articulated stylet, and which may rotate or articulate the articulated stylet.
Figure 8B:
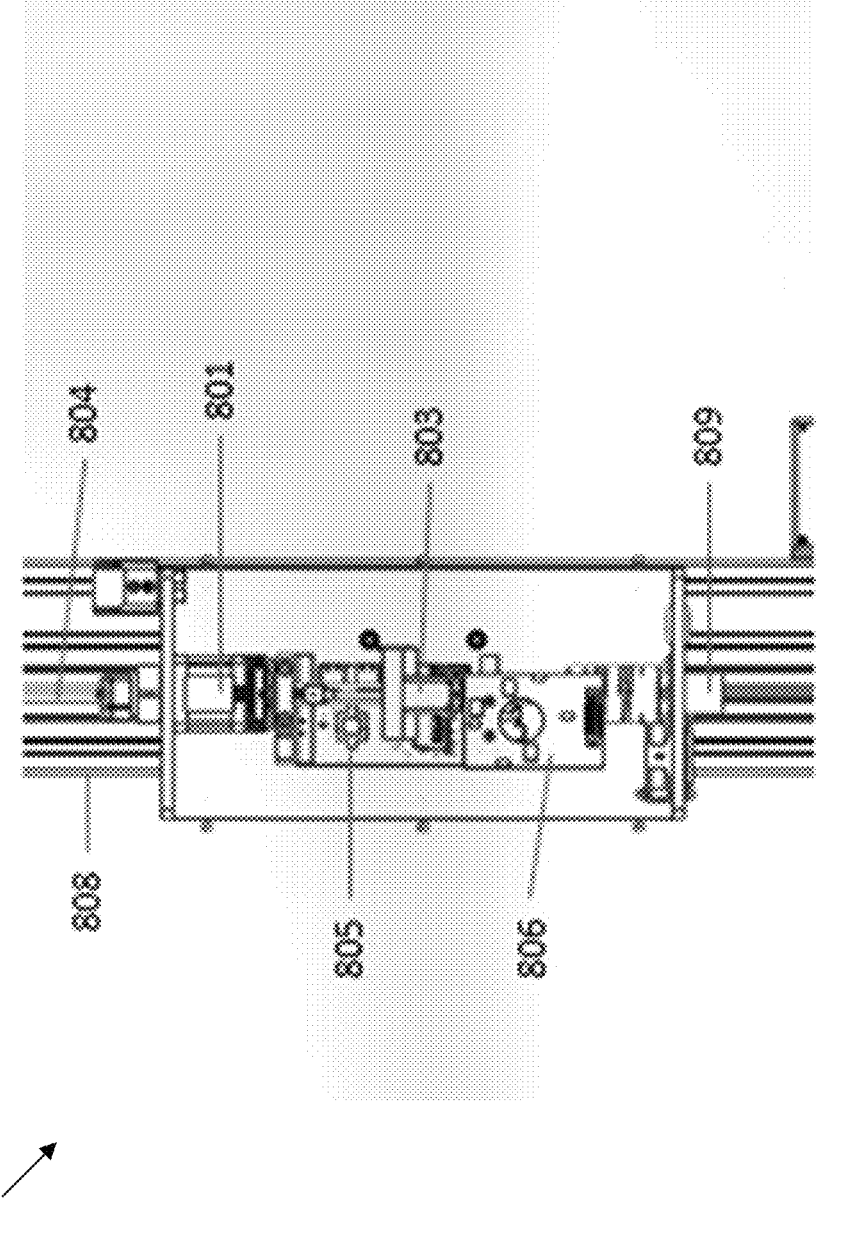

FIGS. 8A and 8B show perspective and top-down views, respectively, of the interior details of the carriage 701 of FIG. 7. The example carriage interior 800 contains motors to control the rotation and tip actuation of the articulated stylet 804 (e.g., articulated stylet 702, FIG. 7). The motors of the present example may allow control of the articulated stylet 804 with 3 degrees of freedom which would be the least number needed to navigate the tract. More degrees of freedom may be added to increase the number of articulated joints or change the contour or shape as the articulated stylet 804 is navigated/driven to a target location. The rotation of the articulated stylet 804 is controlled by a rotation motor 801, while the actuation of the tip of the articulated stylet 804 is controlled by a pull wire motor 803. The carriage (e.g., carriage 701, FIG. 7) moves along the linear slide 808 (e.g., slide 703, FIG. 7) controlled by a linear slide motor 802. The rotational motor 801 may also rotate a center shaft inside the carriage. A camera 805 and a light source 806 may be mounted on the center shaft. The camera 805 and the light source 806 may rotate with the articulated stylet 804 to allow for implantation of an image guide (e.g., image guide 903, FIG. 9) and light pipe (e.g., light pipe 904, FIG. 9). The camera 805 and light source 806 may utilize a variety of wavelengths of illumination, or imaging methodologies, including topographical imaging, time of flight imaging, and/or still and/or video visual (e.g., 2D) imaging. The shaft 809 may be capable of continuous 360 degree rotation without binding any of the necessary wiring to power or communication with the camera 805 or light source 806.

Figure 9:
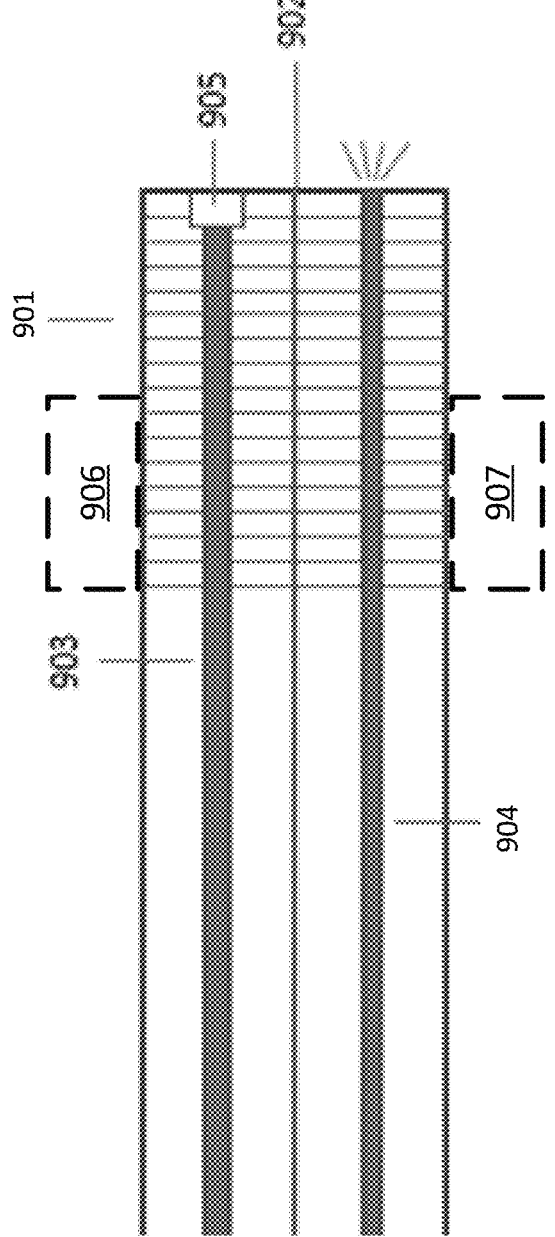
FIG. 9 illustrates an exemplary cross section of an articulated stylet which may feature an image guide, light pipe, and a bending section with a pull wire for articulation.

FIG. 9 shows a lateral cross section of an exemplary articulated stylet 900. The articulated stylet 900 has a bending section 901 at its distal tip. The bending section is attached to a pull wire 902 that can be actuated by a pull wire motor (e.g., pull wire motor 803, FIGS. 8A and 8B). The Enhanced Articulated Stylet may also include an image guide 903 with lensing 905. The image guide 903 provides a pathway by which optical data received through the lensing 905 may be passed back to the camera (e.g., camera 805, FIGS. 8A and 8B) within a carriage (e.g., carriage 701, carriage interior 800, FIGS. 7, 8A, and 8B). Illumination for the camera is provided through the light pipe 904, which connects back to a light source (e.g., light source 806, FIGS. 8A and 8B) in the carriage. In some embodiments, the image guide 903 and a light bundle that includes the light pipe 904 may additionally or alternatively be embedded within a catheter tube (e.g., a catheter tube 100, 200, 500 of FIGS. 1A, 2, 5A) external to the articulated stylet 900 (e.g., into which the articulated stylet 900 is inserted). In some embodiments, the articulated stylet 900 may include a stylet spectrometer 906 and/or a stylet transceiver 907 at or near the distal end (FIG. 9).

A potential embodiment of the RCDC 700 of FIG. 7 utilizes the continuous rotation mechanism 809 of FIGS. 8A and 8B to wire local components held within the carriage 701 back to a centralized processing and/or display unit (e.g., display 414, FIG. 4A).

Figure 10:
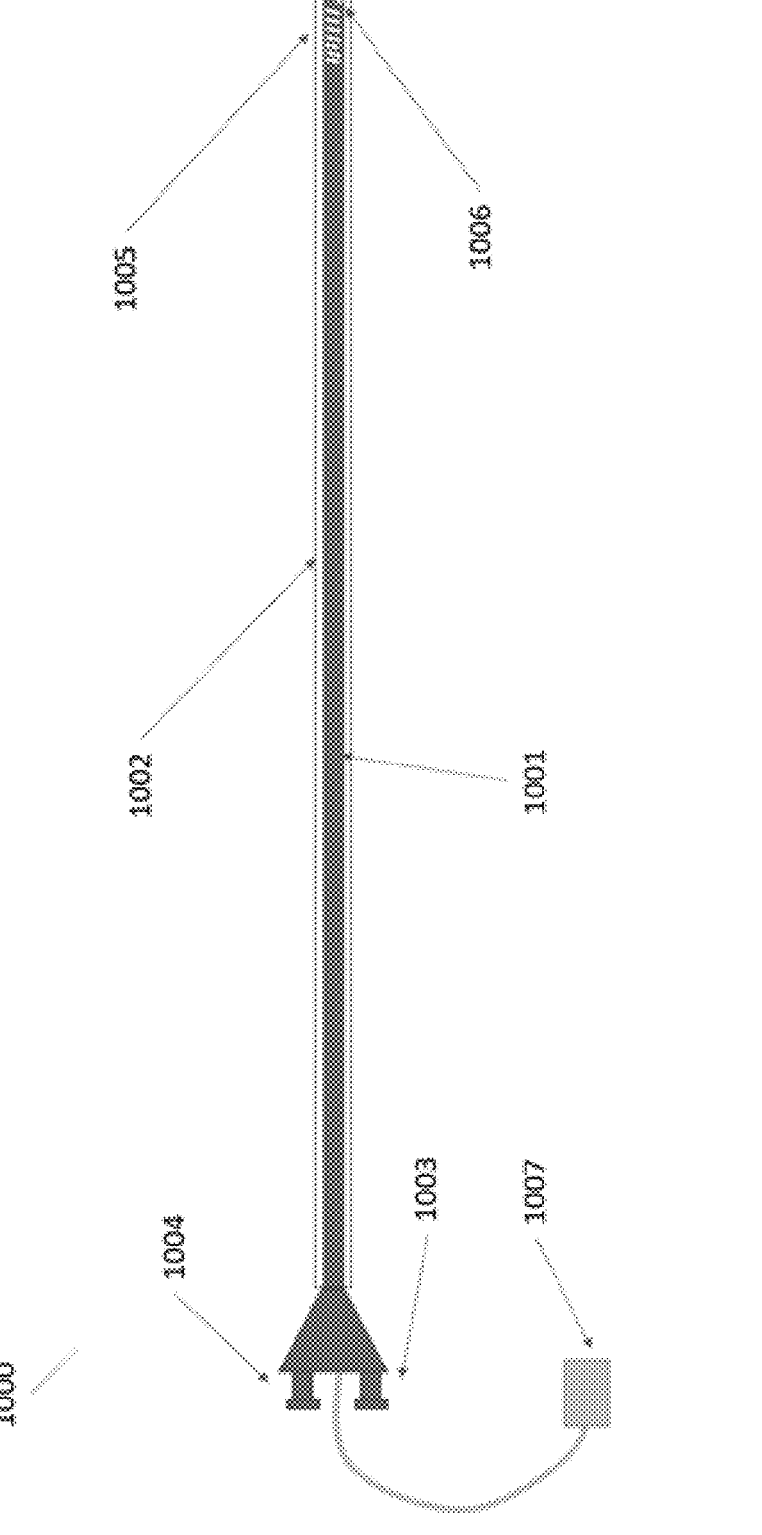
FIG. 10 illustrates an exemplary articulated stylet that has been inserted into a catheter tube, and which includes proximal connection ports that may enable enteral access and/or insufflation, and which includes a proximal optical connector for imaging.

FIG. 10 shows an exemplary assembly 1000 that includes an articulated stylet 1001 that has been inserted into a catheter tube 1002. The articulated stylet 1001 contains a distal bending section 1005, and an optical window 1006. The optical window may connect to an image guide (e.g., image guide 903, FIG. 9), and connect back to a RCDC (e.g., RCDC 400, 700, FIGS. 4A, 4B, and 7) via the optical connector 1007. In some embodiments, optical components may additionally or alternatively be embedded within the wall of the catheter tube 1000 (e.g., catheter tube 100, 200, 500, 1002, of FIGS. 1A, 2, 5A, 10). The catheter tube 1002 has the articulated stylet 1001 inserted into it, and may remain indwelling within the enteral cavity or respiratory tract of the patient after the articulated stylet 1001 is removed. The articulated stylet 1001 may also include a proximal insufflation port 1003 and proximal enteral access port 1004. Both of the ports 1003 and 1004 provide the RCDC access to an embedded lumen, which may be embedded within either the articulated stylet 1001 or the catheter tube 1002.

FIG. 11 shows an illustrative placement of an articulated stylet 1118 (e.g., articulated stylet 420, 502, 702, 804, 900, 1001, FIGS. 4A, 5A, 5B, 7, 8A, 8B, 9, 10) within the colon of a subject. As shown, the articulated stylet 1118 may enter the anus 1102, pass through the rectum 1104, pass through the sigmoid colon 1106, pass thorough the descending colon 1108, pass through the transverse colon 1110, and pass through the ascending colon 1114 to reach a target location. As shown, transitions from the rectum 1104, to the sigmoid colon 1106, from the sigmoid colon 1106 to the descending colon 1108, from the descending colon 1108 to the transverse colon 1110, and from the transverse colon 1110 to the ascending colon 1114 may be made via articulations of the stylet 1118. The distal end 1112 of the articulated stylet 1118 may be located at the target location, and may include an imaging device (e.g., imaging device 108, 208, FIGS. 1A, 1E, AND 2). The imaging device may capture image data (e.g., topographic, time of flight, and/or visual image data) of structures, contents, interior walls, and/or the like of or within the colon as the articulated stylet 1118 traverses the colon, and the image data may be stored in a computer memory device of or communicatively coupled to a robotic control device (e.g., RCDC 400, 700, FIGS. 4A, 4B, 7). The captured image data may be analyzed in real or near-real time as the articulated stylet 1118 traverses the colon to the target location. The robotic control device may be coupled to a proximal end 1116 of the articulated stylet 1118, and may control the plunge, rotation, tip deflection, and advancement/retraction of the articulated stylet 1118.

The catheter tube and RCDC described above may have a variety of practical applications.

In one example application, the catheter tube and RCDC may be applied together for automated gastro-intestinal tract in vivo direct catheter tube navigation for identification, imaging and potential sampling of abnormal tissue samples.

In another example application, the catheter tube and RCDC may be applied together for automated gastro-intestinal tract in vivo direct catheter tube navigation for surveillance of abnormal tissue samples.

In another example application, the catheter tube and RCDC may be applied together for automated lower intestinal tract in vivo direct catheter tube navigation for surveillance of abnormal tissue samples, obtaining topographic or visual image data to be stored at a computer memory of or communicatively coupled to the RCDC, which can be analyzed simultaneously by one or more AI models/algorithms or subsequently by qualified personnel for identification of abnormal tissue in the enteral cavity.

In another example application, the catheter tube and RCDC may be applied together for automated gastro-intestinal tract in vivo direct catheter tube navigation for sampling of biomarkers for gastro-intestinal cancer, inflammatory disease, and malabsorption syndromes.

In another example application, the catheter tube and RCDC may be applied together for automated gastro-intestinal tract in vivo direct catheter tube navigation for assistance in operative procedures including percutaneous feeding access, and/or various laparoscopic interventions including endoscopic bariatric surgery, and endoscopic surgery of biliary tracts.

In another example application, the catheter tube and RCDC may be applied together for automated respiratory tract in vivo direct endotracheal intubation tube navigation for automated intubation.

In another example application, the catheter tube and RCDC may be applied together for automated respiratory tract in vivo direct endotracheal intubation tube navigation for ventilatory support.

In this embodiment, the use of an automated, autonomous, mobile robot for endotracheal intubation could be critical. This can be accomplished using visual based data and advanced data analytics and artificial intelligence as disclosed herein to drive the device that allows for early, safe, and dependable endotracheal intubation.

In this embodiment the stylet of the robot extending from the RCDC would be placed through one end of the endotracheal tube to be inserted and brought out the other end. The stylet would then be placed either in the nostril of the patient (either the left or right nostril) or in the mouth of a patient (alongside a standard oral-pharyngeal tube). The robot would at this point start its process. Using images obtained from the visual and topographic cameras at the tip of the stylet, the computer's algorithm would begin to recognize structure in the nasopharynx or oropharynx (depending on the site of insertion) and given these images the robot would direct the stylet down the pharynx into the larynx. At this point the epiglottis will come into the sight of the robot, which will be recognized. The algorithm will recognize the juncture of the larynx anteriorly and the esophagus posteriorly and through the use of the actuators and motors that control all of its degrees of freedom, steer the stylet anteriorly through the larynx and through the vocal chords into the trachea. This will all be done using computer vision as a guide, without input required from any clinician at the patient's side. The decisions guiding the direction of the stylet will all be automated through the computer algorithm and controlled through the mechanical system of the device.

Once in the trachea, the device will provide images of the inside of the trachea. It will be able to give confirmatory evidence of the correct placement of the stylet in the trachea, through the vocal cords and above the level of the division of the trachea into mainstem bronchi, known as the carina. This is critical as it will confirm the position of the stylet through identification of the vocal cords therefore ensuring a secure airway, but will not be placed so deep as to create intubation of one of the bronchi that could cause ventilation of only one lung.

In one embodiment, this confirmation could be provided as a live photograph to the clinicians at the patient's side or a three-dimensional topographic reconstruction.

In one embodiment, placement of the endotracheal stylet can be confirmed to be in the airway by the use of a stylet spectrometer 906 (FIG. 9) similar to the previously described spectrometer which is attached to a distal end of the stylet along with a stylet transceiver 907 (FIG. 9) and which can be used to detect carbon dioxide in the specimen being sampled. The detection of carbon dioxide provides an indication that the stylet is in the airway as opposed to in the esophagus, where no carbon dioxide would be expected to be detected. This would be a second form of confirmation of proper placement (along with identification of the vocal cords).

The correct placement of the endotracheal tube is critical as an incorrectly placed endotracheal tube is a major complication that can expose patients to a prolonged period with low oxygenation and tissue ischemia.

Once the stylet has been confirmed to be in the correct location, both through the use of visual images or three dimensional image reconstructions, as well as through the use of spectroscopic identification of intraluminal carbon dioxide, the endotracheal tube which is placed over the outside of the robotic stylet will simply be advanced over the stylet into the correct placement in the patient trachea.

FIG. 12A shows a diagram of the robotic control center 1200 advancing the catheter device with its inner articulated stylet 1210 and the exterior catheter tube 1220, demonstrating the self-driving robot advancing to the inflection point of the larynx where the robot can turn anteriorly into the larynx and trachea or posteriorly into the esophagus. At this point, the computer algorithm, basing its decisions on the images obtained from the cameras on the robot's stylet, will guide the mechanical part of the robotic control to turn the stylet anteriorly in the pharynx into the larynx, through the vocal cords and into the trachea.

FIG. 12B shows a diagram of the robot advancing the catheter device with the inner articulated stylet, and the exterior catheter tube, demonstrating the self-driving robot advancing beyond the inflection point of the pharynx having driven anteriorly into the larynx and trachea for pulmonary access.

FIG. 12C shows a diagram of the robot advancing the catheter device with its inner articulated stylet, and the exterior catheter tube, demonstrating the self-driving robot advancing to the point beyond the inflection point of the pharynx having driven posteriorly into the esophagus for upper enteral access.

EXAMPLE

The following is a non-limiting example in accordance with embodiments of the invention.

Experimental Data Support

The process of the autonomous endotracheal tube insertion was validated by dividing it into two individual parts: an object detection functionality that guides the robot and an integrated system that controls the robot individually.

Image Dataset (for Robot Guidance Experiment) and Phantom Model (for Robot Control Experiment)

A commercially available training model, Koken Model for Suction and Tube Feeding Simulator: LM-097B (Koken Co Ltd, Bunkyo-ku, Japan), was purchased for experimentation. The images used for training of the model in tracheal detection were obtained utilizing this phantom. These images were obtained by manual control and automatic control of the robot during image/data gathering.

System Configuration

Figure 13:
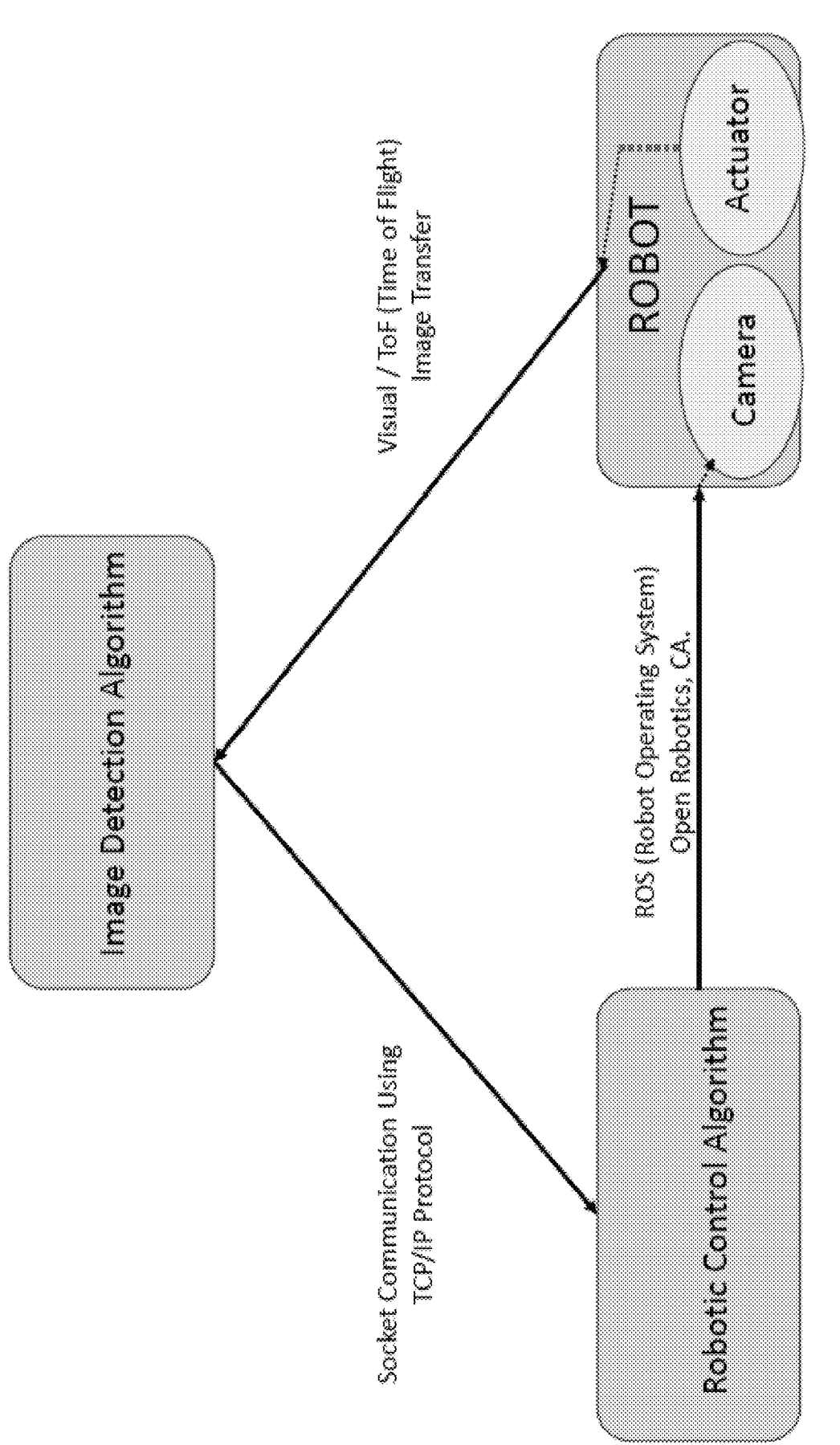
FIG. 13 shows a system configuration in which the image detection computer receives the visual feedback from the robot's camera located on the distal end of the stylet. The image detection algorithm processes the data and recognizes the anatomical landmarks of the image. This data is sent to the robotic control computer where the robotic control algorithm processes instructions for movement according to the anatomic location of the robot's stylet. The robot is controlled by the robot control computer via ROS communication. The robot control computer receives input from image detection computer to adjust control.

A macroscopically one-way closed loop system was built, consisting of 1) robot, 2) robot controlling computer, and 3) tracheal detection computer. The robot was controlled with communication based on ROS™ (Open Robotics, Mountain View, CA and Symbiosis, Singapore) from the robot controlling computer. The robot controlling computer transitioned between multiple modes based on the information provided by the trachea detection computer via primitive socket communication. The trachea detection computer received stream images from the camera which the robot carried (FIG. 13).

Robot Guidance

An AI based detection and tracking model was developed which enables the robot to traverse autonomously using the real-time captured images. The objective is to first detect the trachea opening from the images and then follow the path predicted by a detection-tracking based mechanism. For detection, a deep learning-based detector (YOLO) was trained to detect the trachea, by further distinguishing between the esophageal and tracheal openings. For tracking, we specifically use a fast and computationally efficient median filtering technique.

A. Trachea Detection

Convolutional neural network (CNN) based detectors have achieved a state-of-the art performance for real-time detection tasks. Different from traditional methods of pre-defined feature extraction coupled with a classifier, these convolutional neural network-based detection algorithms are designed by a unified hierarchical representation of the objects that are learned using the imaging data. These hierarchical feature representations are achieved by the chained convolutional layers which transform the input vector into a high dimensional feature space. For esophageal detection, we used a 26-layer CNN-based detection model. The first 24 layers are fully convolutional layers are pre-trained on an Imagenet dataset and the last two layers are fully connected layers which output the detected regions. Our variant of the 26-layer CNN-based detection model is fine-tuned with the colored images of the nasogastric regions.

B. Tracking

A median flow filtering based tracking technique was designed to predict the motion vector for the robotic tube, where median filtering in a classical tracking technique.

C. Robotic Control

The object detection via YOLOv3 and the object tracking via median flow tracker was implemented with Python 3.7.6. The environment was built on Ubuntu 18.04. As for Graphics Processing Unit (GPU) integration, cuDNN 7.6.5 and CUDA toolkit 10.0 were served for use.

The training part was implemented by feeding the annotated image to Keras implementation of YOLOv3. The version for Keras was 2.2.4 and this version runs Tensor-Flow 1.15 on the backend. The dataset was created with an annotation software, VoTT R (Microsoft, Redmond, WA).

Figure 15:
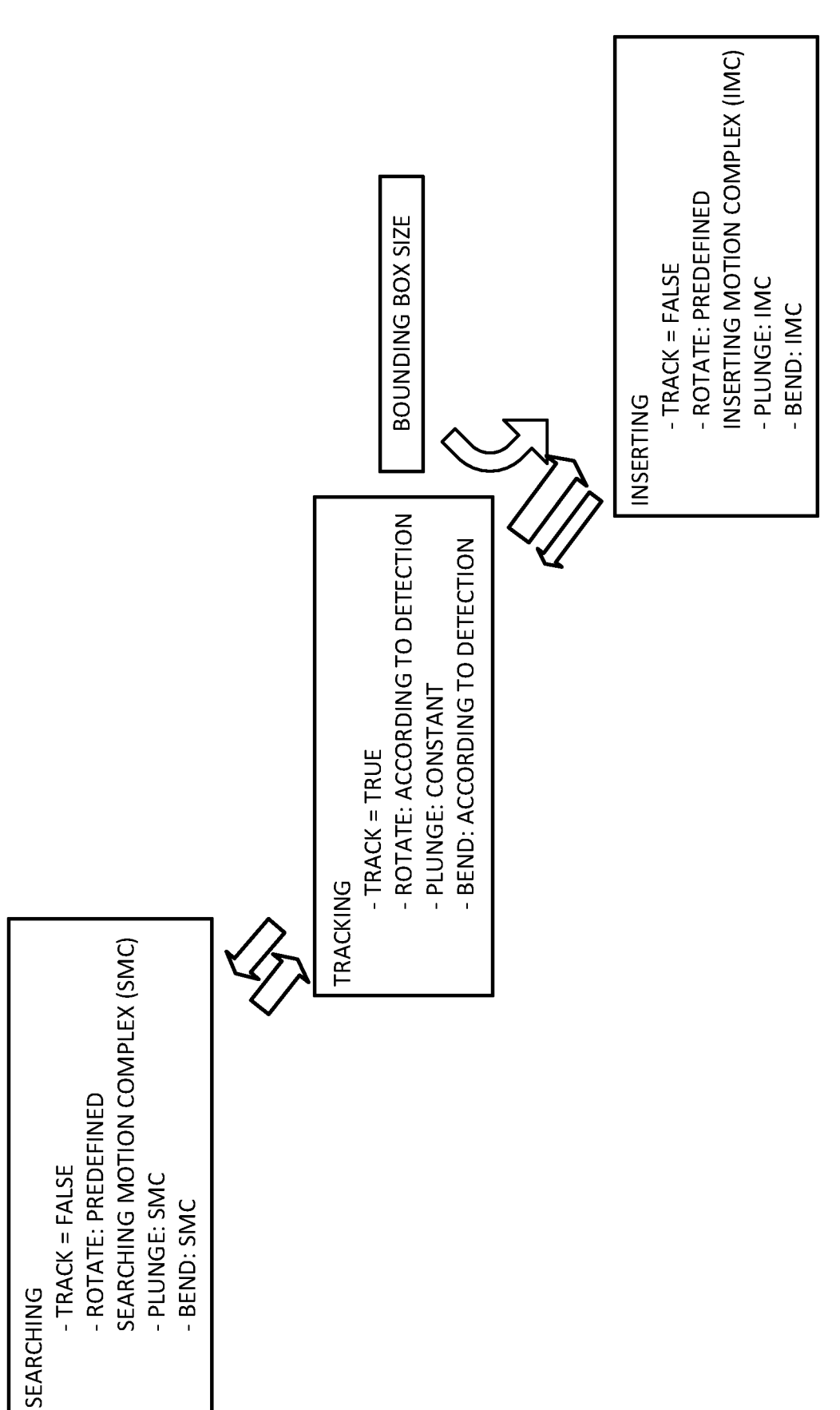
FIG. 15 shows a diagram of a robot control scheme, in particular a schematic drawing of the robot control algorithm. The robot is controlled based on the tracking information received from the image detection computer.

We adopted a learning rate for 1000 training epochs and saved the model parameters every 100 epochs. Among the saved models, the one that achieved the highest Average Precision (AP) for Intersection over Union (IoU) of 50% or higher was considered as positive on the validation set and was therefore selected as the final model to be evaluated on the testing set. The detection part was also implemented based on Keras 2.2.4 running TensorFlow 1.15 on the backend. As for the tracking part, tracking API in OpenCV 4.1.0 was used. The bounding box detected by YOLOv3 was passed to Median Flow tracker at a 1:5 ratio, thereby realizing real-time detection, tracking and control using two families of algorithms (FIGS. 14A, 14B). The distance of the robot to the trachea was approximated by the size of the detected bounding box. A transitioning strategy was built between certain modes each aimed at searching the trachea, tracking the trachea, and inserting the guide into the trachea, respectively (FIG. 15).

Experimental Model

The system was evaluated by dividing the robotic endotracheal intubation process into two individual phases. One is guidance and detection and the other is control.

Robot Guidance Validation

An evaluation was conducted to determine whether the CNN-based object detection of our system can detect real trachea. Endoscopic images with clearly open trachea and clearly closed trachea with more than two thirds of the aspect is visible were picked. The obtained images were incorporated into the YOLOv3 training described earlier in the Robot Guidance section.

Accuracy in recognizing the trachea compared to human recognition was evaluated using mean Average Precision (mAP) and Average Precision (AP). Additionally, Precision-Recall curve for each detection class was depicted.

Robot Control Validation

Here, it was evaluated if the robot can control itself to the trachea. The training was conducted in an identical way as the Robot Guidance Validation experiment. It was evaluated if an endotracheal tube can actually travel over the robot through to the trachea by comparing the success rate of the tube reaching trachea with and without robot inside the trachea.

The success rate of the endotracheal tube in reaching the trachea was evaluated using a commercially-available endotracheal tube with an inner diameter of 7 mm.

Results

A statistical analysis was utilized for the tube insertion part of the robot control validation experiment to evaluate the significance of the difference in the success rate between the proposed method and internal controls. Statistical analysis was conducted by Prism (GraphPad Software, San Diego, CA). Significance cutoff point was set to be 0.05. Power analysis was conducted to optimize the number of trials that were necessary for each experimental setup based on pilot experiments.

Robot Guidance Validation Experiment

Accuracy of the detection with regard to mAP and AP were assessed for each datasets. The program algorithm demonstrated ability to detect the trachea in the closed configuration (97%) and in the opened configuration (100%).

Robot Control Validation Experiment

The success rate of the robot to travel to the trachea was 96.7% (29/30) for fully integrated detection based control for fully the integrated detection based control, vs. 6.7% (2/30) for blind manual insertion, respectively.

Many modifications and variations to this preferred embodiment will be apparent to those skilled in the art, which will be within the spirit and scope of the invention. Therefore, the invention should not be limited to the described embodiment. To ascertain the full scope of the invention, the following claims should be referenced.

What is claimed is:

1. A system for automated, self-navigating placement of a catheter tube in a respiratory tract of a subject, the system comprising:

the catheter tube comprising:

a tube wall that defines a lumen;

an imaging device configured to capture image data, the imaging device disposed at a distal end of the catheter tube, the imaging device configured to capture the image data from within the respiratory tract in real time;

a spectrometer disposed at the distal end of the catheter tube, the spectrometer configured to capture spectrometer data from within the respiratory tract in real time; and a transceiver coupled to the imaging device and the spectrometer and configured to wirelessly transmit the captured image data and the captured spectrometer data in real time, the transceiver disposed at the distal end of the catheter tube;

an articulated stylet disposed in the lumen of the catheter tube, the articulated stylet comprising an articulated distal end; and a robotic control and display center comprising:

wireless communication circuitry that communicates with and receives the captured image data and the captured spectrometer data from the transceiver in real time;

processing circuitry configured to execute at least one artificial intelligence model configured to navigate the respiratory tract without manual input, where the at least one artificial intelligence model:

analyzes the real-time captured image data to identify orifices and structures within the respiratory tract and assigns bounding boxes to the identified orifices and structures, provides the assigned bounding boxes to a median-flow filtering module configured to predict a motion vector of the articulated stylet using sparse flow, determines navigation data based on at least one of the captured image data, the assigned bounding boxes, or the predicted motion vector, outputs the corresponding navigation data to a robotic control engine in real time, analyzes the real-time captured spectrometer data, identifies a biomarker to which the capture spectrometer data corresponds, wherein the biomarker is identified based on absorbance and/or percent transmittance of the captured spectrometer data and a corresponding chemical composition of the biomarker, and displays information related to the biomarker; and the robotic control engine configured to drive the articulated stylet, without manual guidance, toward a target destination inside the respiratory tract based on the navigation data determined by the artificial intelligence model, wherein the navigation data comprises instructions to at least one of manipulate, articulate, rotate, or drive the articulated stylet.

2. The system of claim 1, wherein the imaging device comprises a topographic imaging device, and wherein the captured image data comprises topographic image data.

3. The system of claim 2, wherein the imaging device further comprises a visual imaging device, and wherein the captured image data further comprises visual image video data.

4. The system of claim 1, wherein the imaging device and the transceiver are embedded in the tube wall of the catheter tube, and wherein the catheter tube further comprises:

an insufflating channel embedded in the tube wall of the catheter tube; and a light source embedded in the tube wall of the catheter tube.

5. The system of claim 1, wherein the imaging device comprises a time-of-flight imaging device, wherein the captured image data further comprises time-of-flight image data, and wherein the time-of-flight imaging device is configured to capture the time-of-flight image data using multiple wavelengths of light.

6. The system of claim 5, wherein the processing circuitry is further configured to execute a volume sensing module configured to:

obtain volume measurements of an enteral space in which the catheter tube is disposed based on three-dimensional volumetric data generated via a technique selected from the group consisting of: hyperspectral imaging, time of flight imaging, and stereo imaging;

determine, based on the volume measurements, a first volume value corresponding to a total volume of the enteral space;

determine, based on the volume measurements, a second volume value corresponding to a first portion of the total volume that is empty; and determine, by subtracting the second volume value from the first volume value, a third volume value of a second portion of the total volume that is filled with material.

7. The system of claim 1, wherein the robotic control engine is configured to drive the articulated stylet by controlling at least one articulation of the articulated stylet to control a direction of movement of the articulated stylet, the articulated stylet having three degrees of freedom including plunge, rotation, and tip deflection.

8. The system of claim 1, wherein the at least one artificial intelligence model comprises:

a detection and tracking model that processes the captured image data in near-real time;

a deep-learning detector configured to analyze the captured image data to identify the orifices and structures within the respiratory tract and assign the bounding boxes to the identified orifices and structures, wherein the deep-learning detector comprises at least one convolutional-neural-network-based detection algorithm that is trained to learn unified hierarchical representations, that identifies the orifices and structures based on the captured image data, and that calculates the navigation data based on the captured image data and the target destination; and the median-flow filtering based visual tracking module configured to predict the motion vector of the articulated stylet using sparse optical flow.

9. The system of claim 1, wherein the imaging device and the transceiver are embedded in the articulated stylet wherein the articulated stylet further comprises:

an insufflating channel embedded in the articulated stylet; and a light source embedded in the articulated stylet.

10. The system of claim 1, wherein the biomarker comprises at least one of sodium, potassium, osmolarity, pH, a medication, a digestive enzyme, a lipid, a fatty acid, blood, or a blood product.

11. The system of claim 1, wherein the biomarker is produced by an organ of the subject.

12. The system of claim 1, wherein the biomarker is identified without use of a contrast dye or other labeling agent.

13. A robotic control and display center for use in automated, self-navigating placement of a catheter tube in a respiratory tract of a subject, the robotic control and display center comprising:

wireless communication circuitry that communicates with and receives topographical image data and captured spectrometer data obtained from within the respiratory tract in real-time from a transceiver of the catheter tube in real time, the catheter tube comprising an articulated stylet disposed in a lumen of the catheter tube;

processing circuitry configured to execute an artificial intelligence model configured to navigate the respiratory tract without manual input, where the artificial intelligence model:

analyzes the real-time captured topographical image data to identify orifices and structures within the respiratory tract and assigns bounding boxes to the identified orifices and structures and a target destination, provides the assigned bounding boxes to a median-flow filtering module configured to predict a motion vector of the articulated stylet using sparse flow, determines navigation data based on at least one of the captured image data, the assigned bounding boxes, or the predicted motion vector, outputs the corresponding navigation data to a robotic control engine in real time, analyzes the real-time captured spectrometer data, identifies a biomarker to which the captured spectrometer data corresponds, wherein the biomarker is identified based on absorbance and/or percent transmittance of the captured spectrometer data and a corresponding chemical composition of the biomarker, and displays information related to the biomarker; and the robotic control engine configured to automatically and without manual guidance drive the articulated stylet disposed inside the catheter tube toward the target destination inside the respiratory tract based on the navigation data determined by the artificial intelligence model, wherein the navigation data comprises instructions to at least one of manipulate, articulate, rotate, or drive the articulated stylet.

14. The robotic control and display center of claim 13, wherein the robotic control engine is configured to control a direction of movement of the articulated stylet by controlling one or more of plunge, rotation, or deflection of an articulation in a distal end of the articulated stylet.

15. The robotic control and display center of claim 13, wherein the spectrometer data corresponds to a substance sampled by a spectrometer of the catheter tube, and wherein the processing circuitry is configured to execute an additional artificial intelligence model that receives the spectrometer data and outputs an identity of the biomarker to which the substance corresponds.

16. The robotic control and display center of claim 15, further comprising:

a display device that is configured to display information related to a location and status of the catheter tube and the identity of the biomarker.

17. A catheter assembly for automated, self-navigating placement of a catheter tube in a respiratory tract of a subject, the catheter assembly comprising:

the catheter tube comprising:

a tube wall that defines a lumen;

an imaging device configured to capture image data, the imaging device disposed at a distal end of the catheter tube, the imaging device configured to capture the image data from within the respiratory tract in real-time;

a spectrometer configured to capture spectrometer data from within the respiratory tract in real time, the spectrometer disposed at the distal end of the catheter tube, wherein the captured spectrometer data is used to identify a biomarker based on absorbance and/or percent transmittance of the captured spectrometer data and a corresponding chemical composition of the biomarker;

a transceiver coupled to the imaging device and configured to wirelessly transmit the captured image data to a remote computer system in real time, the transceiver being disposed at the distal end of the catheter tube; and an articulated stylet disposed in the lumen, the articulated stylet configured to be automatically driven to a target location within a subject without manual guidance and based on at least the real-time captured image data, the articulated stylet having three degrees of freedom including plunge, rotation, and tip deflection, and each degree of freedom in the three degrees of freedom being independently controllable, wherein the remote computer system is configured to execute at least one artificial intelligence model configured to navigate the respiratory tract without manual input, where the at least one artificial intelligence model:

analyzes the real-time captured image data to identify orifices and structures within the respiratory tract and assign bounding boxes to the identified orifices and structures, provides the assigned bounding boxes to a median-flow filtering module configured to predict a motion vector of the articulated stylet using sparse flow, determines navigation data based on at least one of the captured image data, the assigned bounding boxes, or the predicted motion vector, and outputs the corresponding navigation data to the transceiver in real time.

18. The catheter assembly of claim 17, wherein the spectrometer is configured to sample and analyze substances proximal to the distal end of the catheter tube to produce spectrometer data, wherein the transceiver is configured to wirelessly transmit the spectrometer data to the remote computer system.

19. The catheter assembly of claim 18, wherein the imaging device, the spectrometer, and the transceiver are each embedded at different locations in the tube wall of the catheter tube, wherein the catheter tube further comprises:

an insufflation channel embedded in the tube wall.

20. The catheter assembly of claim 17, wherein the image data comprises topographical image data depicting structures proximal to the imaging device.

* * * * *